United States Patent
Dae et al.

(10) Patent No.: US 6,582,457 B2
(45) Date of Patent: Jun. 24, 2003

(54) METHOD OF CONTROLLING BODY TEMPERATURE WHILE REDUCING SHIVERING

(75) Inventors: Michael W. Dae, Belmont, CA (US); Timothy R. Machold, Moss Beach, CA (US); Wade A. Keller, San Jose, CA (US)

(73) Assignee: Radiant Medical, Inc., Redwood City, CA (US)

( * ) Notice: Subject to any disclaimer, the term of this patent is extended or adjusted under 35 U.S.C. 154(b) by 93 days.

(21) Appl. No.: 09/784,930

(22) Filed: Feb. 15, 2001

(65) Prior Publication Data

US 2002/0111657 A1 Aug. 15, 2002

(51) Int. Cl.$^7$ .................................. A61F 7/12
(52) U.S. Cl. .......................... 607/113; 607/96; 604/500; 604/506; 604/503; 514/12; 514/649; 514/396; 514/215; 514/429
(58) Field of Search ........................... 607/113, 96, 106, 607/105, 104, 103; 514/12, 649, 396, 215, 429; 604/500, 506, 503, 28

(56) References Cited

U.S. PATENT DOCUMENTS

| | | | |
|---|---|---|---|
| 4,544,664 A | * 10/1985 | Karjalainen et al. | 514/396 |
| 4,758,561 A | 7/1988 | Le Baut et al. | |
| 4,758,562 A | * 7/1988 | Adler et al. | 514/224.8 |
| 5,120,713 A | * 6/1992 | Mugica | 514/17 |
| 5,486,204 A | 1/1996 | Clifton | |
| 5,486,208 A | * 1/1996 | Ginsburg | 607/106 |
| 5,654,439 A | * 8/1997 | Pandey et al. | 548/406 |
| 5,679,649 A | * 10/1997 | Fukunaga | 514/46 |
| 5,821,219 A | * 10/1998 | Grandy et al. | 514/2 |
| 5,863,934 A | * 1/1999 | Arnsten et al. | 514/401 |
| 6,110,168 A | * 8/2000 | Ginsburg | 606/27 |
| 6,149,673 A | * 11/2000 | Ginsburg | 607/96 |
| 6,156,057 A | * 12/2000 | Fox | 607/96 |

(List continued on next page.)

FOREIGN PATENT DOCUMENTS

| WO | WO 98/26831 | 6/1998 |
|---|---|---|
| WO | WO 98/31312 | 7/1998 |

OTHER PUBLICATIONS

Chai et al., "Hypothermic Action of Chlorpromazine in Monkeys," Br. J. Pharmac., vol. 57, pp. 43–49, 1976.

Jessen et al., "Intravascular Heat Exchanger for Conscious Goats," Pflugers Arch., vol. 368, pp. 263–265, 1977.

(List continued on next page.)

*Primary Examiner*—Ira S. Lazarus
*Assistant Examiner*—Tu Cam Nguyen
(74) *Attorney, Agent, or Firm*—Robert D. Buyan; Stout, Uxa, Buyan & Mullins, LLP

(57) ABSTRACT

A method and apparatus for lowering the body temperature of a patient while reducing shivering by using a heat exchange device in combination with an α2-adrenoreceptor agonist, a non-opiod analgesic monoamine uptake inhibitor or neuropeptide that temporarily reduces shivering. The devices disclosed include a catheter having a heat exchange balloon thereon with heat exchange fluid circulating through the interior of the balloon. The heat exchange balloon is placed in the vasculature of a patient, and heat exchange fluid at a temperature other than the temperature of the blood in the vasculature is circulated through the interior of the balloon to add or remove heat from the blood of the patient. Various α2-adrenoreceptor agonistα2-adrenoreceptor agonists, non-opiod analgesic monoamine uptake inhibitors and neuropeptides are disclosed including dexmedetomidine, nepofam and neurotensin and pharmaceutically acceptable salts thereof. A control system for the control of the patient's temperature is disclosed for controlling the patient'stemperature in conjunction with administering the α2-adrenoreceptor agonist, non-opiod analgesic monoamine uptake inhibitor or neuropeptide.

23 Claims, 8 Drawing Sheets

U.S. PATENT DOCUMENTS

| | | | | |
|---|---|---|---|---|
| 6,231,594 B1 | * | 5/2001 | Dae | 607/96 |
| 6,288,123 B1 | * | 9/2001 | Goldin et al. | 514/634 |
| 6,299,599 B1 | * | 10/2001 | Pham et al. | 604/113 |
| 6,420,137 B1 | * | 7/2002 | Strnad et al. | 435/69.1 |
| 2002/0111616 A1 | * | 8/2002 | Dae et al. | 606/41 |

OTHER PUBLICATIONS

Mercer et al., "Effects of Total Body Core Cooling on Heat Production of Conscious Goats," vol. 373, pp. 259–267, 1978.

Millan et al., "S18616, a Highly Potent, Spiroimidazoline Agonist at $\alpha_2$–Adrenoceptors: I. Receptor Profile, Antinociceptive and Hypothermic Action in Comparison with Dexmedetomidine and Clonidine," The Journal of Pharmacology and Experimental Therapeutics, vol. 295, No. 3, pp. 1192–1205, 2000.

Piper et al., "Nefopam and clonidine in the prevention of postanaesthetic shivering," Anaesthesia, vol. 54, pp. 695–699, 1999.

Ripstein et al., "A Technique for the Production of Hypothermia," Surgery, vol. 35, No. 1, pp. 98–103, 1954.

Rosa et al., "Control of post anaesthetic shivering with nefopam hydrochloride in mildly hypothermic patients after neurosurgery," Acta Anaesthesiol Scand, vol. 39, No. 1, pp. 90–95, 1995.

Talke et al., "Dexmedetomidine Does Not Alter the Sweating Threshold, But Comparably and Linearly Decreases the Vasoconstriction and Shivering Thresholds," Anaesthesiology, vol. 87, No. 4, pp. 835–841, 1997.

Tyler et al., "In vitro binding and CNS effects of novel neurotensin agonists that cross the blood–brain barrier," Neuropharmacology, vol. 38, pp. 1027–1034, 1999.

Tyler–McMahon et al., "Highly potent neurotensin analog that causes hypothermia and antinociception," Eur J Pharmacol, vol. 390, pp. 107–111, 2000.

* cited by examiner

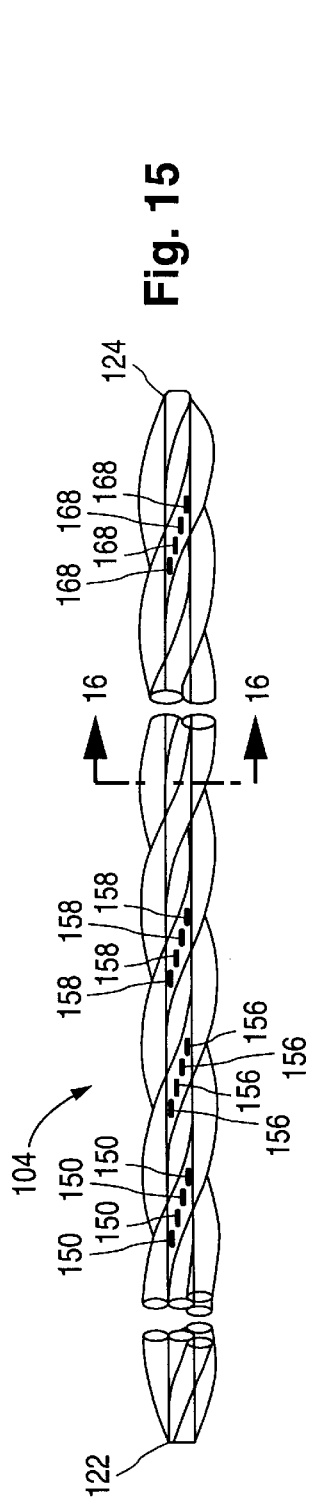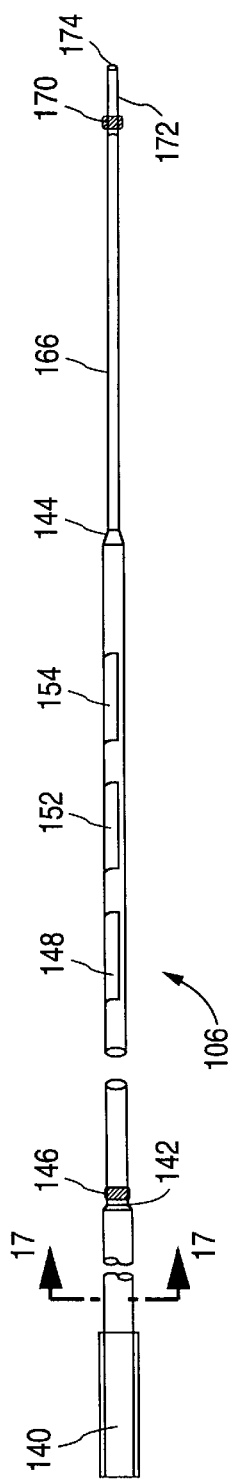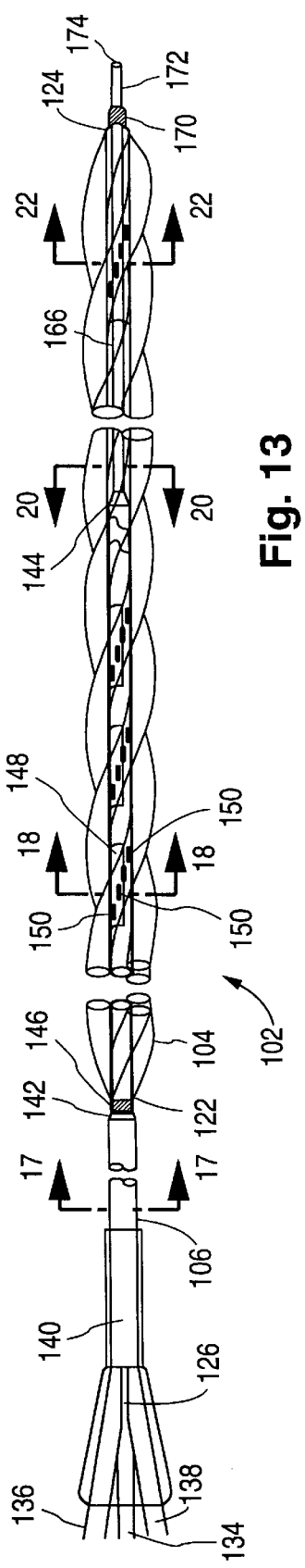

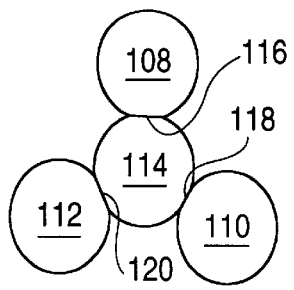 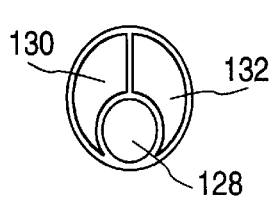 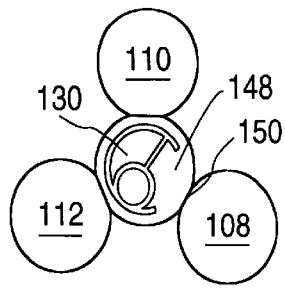
Fig. 16    Fig. 17    Fig. 18
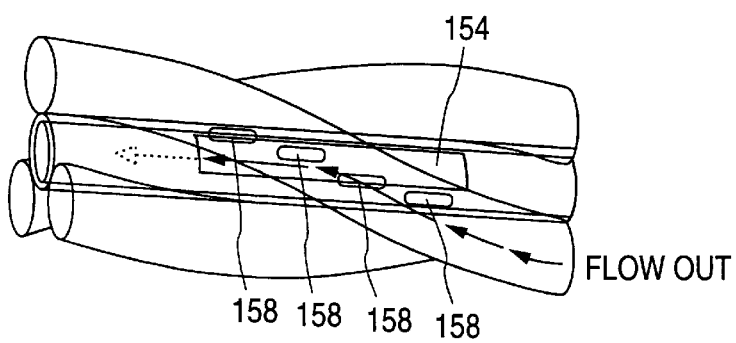 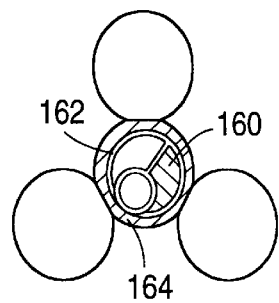
Fig. 19    Fig. 20
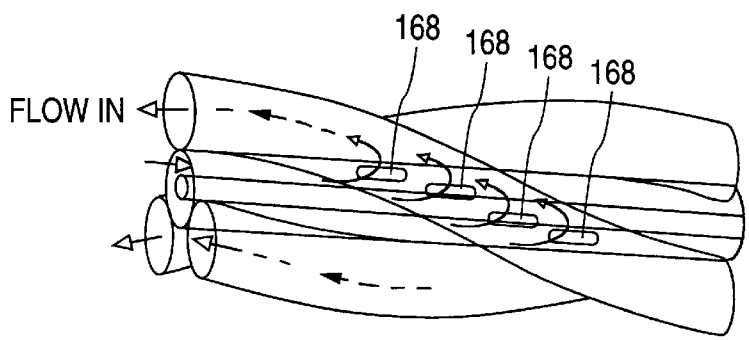 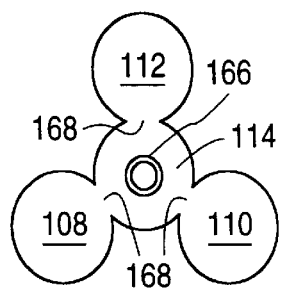
Fig. 21    Fig. 22

METHOD OF CONTROLLING BODY TEMPERATURE WHILE REDUCING SHIVERING

RELATED PATENT APPLICATION

This invention is related to the invention disclosed in the copending, coassigned patent application of Dae, et al., for Method of Controlling Body Temperature While Reducing Shivering, U.S. Ser. No. 09/372,714, filed on Aug. 11, 1999.

TECHNICAL FIELD

This invention relates to a method, apparatus and composition for selectively controlling the temperature of all or a portion of a patient's body by lowering, maintaining or raising the temperature of a body fluid or tissue to affect the temperature of all or part of the patient's body, while reducing shivering that typically accompanies such temperature control. More particularly, the invention relates to a heat exchange device in combination with an anti-shivering mechanism to control the temperature of all of a portion of a patient's body while reducing shivering. The invention also relates to novel compositions that are useful for reducing shivering.

BACKGROUND

The "set point temperature" is the temperature that the body attempts to maintain through the thermoregulatory responses. Under ordinary circumstances, thermoregulatory mechanisms within the human body which include sweating and vasodilation to enhance heat loss, arterio venous ("AV") shunting and vasoconstriction to enhance retaining heat, and shivering to enhance increased generation of body heat, serve to maintain the body at a near constant set point temperature of about 37° C. (98.6° F.), often referred to as "normothermic". However, sometimes the body sets a different set point temperature, for example a patient with a fever has an elevated set point temperature, and these mechanisms can serve to maintain an elevated temperature. In the case of a fever, the set point temperature can be higher than normothermic.

There is a temperature slightly below the set point temperature where the body senses that the body temperature is too low and begins to shiver. This temperature is sometimes referred to as the shivering threshold. As with the set point temperature, the shivering: threshold is not an absolute temperature but varies between individuals and within the same individual depending on his or her condition.

As a result of the thermoregulatory mechanisms, any heat lost to the environment is precisely balanced by heat produced within the body. Accordingly, attempts to control the body temperature below the set point temperature often produce shivering in the patient, as this is the main method of generating additional metabolic heat. Shivering can increase heat production by 200–500% and thus presents a serious obstacle when attempts are made to reduce a patient's body temperature.

The thermoregulatory mechanisms provide a formidable defense when attempts are made to lower the body temperature below the set point temperature, for example, when one attempts to induce an artificially low body temperature (a condition known as hypothermia) by lowering the normothermic 37° C. to a lower temperature state or when one attempts to maintain normothermia by lowering an elevated body temperature to normothermic 37° C. Since there are numerous therapeutic reasons for both inducing hypothermia or inducing normothermia in a patient suffering from an elevated temperature, the thermoregulatory mechanisms must be taken into consideration when designing a therapeutic regimen for controlling the temperature of all or a portion of a patient's body. Indeed, when the patient has a set point temperature that is above normothermic, for example when the patient has a fever, the shivering threshold may actually be above normothermic as well, and thus even an attempt to maintain a patient's temperature to normothermia may result in shivering. In addition, even when the thermoregulatory mechanisms have been overcome, the body temperature may continue to drop, possibly below the desired threshold. This "overshooting" phenomenon can lead to complications. Accordingly, any therapeutic regimen for controlling body temperature preferably does so at a carefully monitored and controlled rate.

It has also been found that in rewarming a patient, either after therapeutic hypothermia or a patient suffering from accidental hypothermia, a very gradual and controlled rewarming rate is desirable. The dramatic generation of metabolic heat due to shivering, particularly in addition to heat added by other means, can result in rapid and uncontrolled rewarming. Therefore therapeutic rewarming at a carefully monitored and controlled rate also requires control over shivering.

Hypothermia may be induced to minimize damage to the brain when a patient has suffered a head injury or stroke, or to minimize damage to heart and brain tissue when a patient has undergone cardiac arrest. It may sometimes also be desirable to induce hypothermia during surgery, especially neurosurgery, once again to minimize tissue damage.

Early techniques involved application of cold to the skin surface or cooling the inspired air, alone or in combination with a compound to inhibit the thermoregulatory center such as chlorpromazine (Ripstein, et al., *Surgery* (35)1:98–103 (1954)). More recently, in situ blood temperature modification using a heat exchange catheter was described in Ginsburg, U.S. Pat. No. 5,486,208 and Ginsburg, WP 98/268831, the disclosures of which are incorporated herein by reference. This in situ procedure lowers the body temperature much faster and maintains the temperature at that lower level more precisely than the cooled skin surface or cooled breathing air methods described above.

There are also drugs which are capable of assisting in lowering body temperature. However, many require toxic doses in order to achieve the desired hypothermic state. Temperature lowering was also allegedly achieved with chlorpromazine, when administered in combination with a refrigeration blanket (Ripstein, et al, supra), and when administered alone (Chai, et al, *Br. J. Pharmac.* 57:43–49 (1976)). However, in both these instances, temperature variation after the chlorpromazine was administered was achieved by external cooling or exposure alone and without any significant control of the degree or rate of body cooling. More recently, hypothermia was allegedly induced in rats with a combination of a K opioid receptor agonist and a dopamine receptor blocker or agonist (Adler, et al., U.S. Pat. No. 4,758,562).

It has been shown that the $\alpha_2$-adrenoreceptor agonists dexmedetomidine and clonidine are able to lower the shivering threshold (Talke, et al., *Anesthesiology* 87(4):835–841, 1997). In this study, patients at a normal temperature were warmed until sweating then cooled until shivering occurred, as the $\alpha_2$-adrenoreceptor agonist was administered. Evaluation of the ability of these agonists and a novel agonist to reduce core temperature were later described in Millan, et al., *The Journal of Pharmacology and Experimental Therapeutics* 295(3):1192–1205, 2000. However, in both these studies, as with chlorpromazine, temperature variation after the adrenoreceptor agonist was administered was achieved with only minor control of the degree or rate of body cooling.

However, in spite of these advances, there continues to be a need to develop a method of safely and temporarily inactivating the shivering response while inducing hypothermia or otherwise reducing the body's temperature below its set point temperature for an extended period of time, or while gently and slowly raising the body's temperature from a hypothermic state.

SUMMARY

The present invention pertains to a method for controlling the temperature of all or a portion of a patient's body to a temperature below its set point temperature, while reducing shivering, comprising the steps of: (a) sensing the temperature of all or a portion of the patient's body; (b) generating a signal based upon the sensed temperature; (c) controlling the temperature of all or a portion of the patient's body based upon the signal; and (d) administering an agent selected from the group consisting of α2-adrenoreceptor agonists, non-opiod analgesic monoamine uptake inhibitors and neuropeptides to the patient.

In one embodiment of the invention, the aforementioned method is utilized to lower a patient's body temperature below its set point temperature while reducing shivering.

In yet another embodiment of the invention, the aforementioned method is utilized to raise a patient's body temperature from an initial temperature below the set point temperature while reducing shivering.

Another embodiment of this invention is to utilize the aforementioned method to raise a patient's body temperature at a predetermined rate while reducing shivering.

Still another embodiment of the invention is to utilize the aforementioned method to slowly and controllably rewarm a hypothermic patient from a temperature below the set point temperature toward normothermia.

Another embodiment of the invention is to utilize the aforementioned method to maintain a patient's body temperature at a stable temperature below the set point temperature while reducing shivering.

Yet another embodiment of the invention comprises controlling a patient's body temperature by placing a heat exchange device having a heat exchange region into the vascular system of the patient and controlling the temperature of the heat exchange region for a sufficient time to affect the temperature of all or a portion of the patient's body, while administering an agent selected from the group consisting of α2-adrenoreceptor agonists, non-opiod analgesic monoamine uptake inhibitors and neuropeptides to the patient.

Still another embodiment of the invention is a method of controlling a patient's body temperature by administering an agent selected from the group consisting of α2-adrenoreceptor agonists, non-opiod analgesic monoamine uptake inhibitors and neuropeptides to the patient while using a heat exchange device that is a catheter and the heat exchange region comprises a balloon on the catheter, the temperature of the balloon being controlled by the circulation of a heat exchange fluid through the interior of the balloon. The catheter may have a shaft for the circulation of heat exchange fluid, where fluid circulates through the shaft and through the interior of the balloon.

Another embodiment of the invention relates to controlling the temperature of all or a portion of a patient's body by using a heat exchange device in combination with an agent selected from the group consisting of α2-adrenoreceptor agonists, non-opiod analgesic monoamine uptake inhibitors and neuropeptides or pharmaceutically acceptable salt thereof.

Yet another embodiment of the invention is a method of controlling the temperature of a patient by using a heat exchange device and administering dexmedetomidine.

Yet another embodiment of the invention is a method of controlling the temperature of a patient by using a heat exchange device and administering nepofam.

Yet another embodiment of the invention is a method of controlling the temperature of a patient by using a heat exchange device and administering neurotensin.

The present invention further comprises a method of controlling a patient's body temperature below its set point temperature with an internal heat exchange device, while simultaneously inactivating the shivering response of the patient.

One embodiment of the invention pertains to a method of controlling the temperature of a patient below the set point temperature comprising the steps of: (a) employing internal in vivo core temperature regulation; and (b) administration of an α2-adrenoreceptor agonist.

In another embodiment of the invention, the step of employing internal in vivo core temperature regulation comprises placing a heat exchange device in the blood vessels of the patient, where the heat exchange device has a heat exchange region which is in contact with the flowing blood of the patient; and controlling the temperature of the heat exchange region for a sufficient time to affect the temperature of the patient, while administering an agent selected from the group consisting of α2-adrenoreceptor agonists, non- opiod analgesic monoamine uptake inhibitors and neuropeptides to the patient.

Yet another embodiment of the invention is a kit for reducing the temperature of a patient comprising a heat exchange device and an agent selected from the group consisting of α2-adrenoreceptor agonists, non-opiod analgesic monoamine uptake inhibitors and neuropeptides. The kit may further comprising a set of instructions for use of the heat exchange device and/or administration of the agent. The kit may also comprise a control system which measures patient body temperature and controls the heat exchange device in response to the body temperature.

These and other embodiments of the invention are achieved by the method, apparatus, kit and composition described herein where a patient's body temperature is lowered, such as by inducing hypothermia, utilizing a heat exchange device in combination with an agent selected from the group consisting of α2-adrenoreceptor agonists, non-opiod analgesic monoamine uptake inhibitors and neuropeptides. Such device can comprise an elongate flexible catheter having a heat exchanger that operates to exchange heat between tissue, blood or other body fluid which flows in or is positioned in heat exchanging proximity thereto.

Further aspects and details of the present invention will become apparent to those of skill in the relevant art upon reading and understanding of the detailed description of preferred embodiments set forth here below. Each of the embodiments disclosed below may be considered individually or in combination with any of the other variations and aspects of the invention.

BRIEF DESCRIPTION OF THE DRAWING

FIG. 13 depicts another embodiment a heat exchange catheter, as assembled.

FIG. 14 shows the shaft member of the catheter assembly of FIG. 13.

FIG. 15 illustrates the balloon configuration of the catheter assembly of FIG. 13.

FIG. 16 is a cross-sectional view of the balloon of FIG. 15 taken along line 16—16.

FIG. 17 is a cross-sectional view of the shaft of FIG. 13 taken along line 17—17.

FIG. 18 is a cross-sectional view of the catheter of FIG. 13 taken along line 18—18.

FIG. 19 is a view of a portion of the catheter of FIG. 13 illustrating outflow of heat exchange fluid.

FIG. 20 is a cross-sectional view of the catheter of FIG. 13 taken along line 20—20.

FIG. 21 is a view of a portion of the catheter of FIG. 13 illustrating inflow of heat exchange fluid.

FIG. 22 is a cross-sectional view of the catheter of FIG. 13 taken along line 22—22.

DETAILED DESCRIPTION

Figure 1:
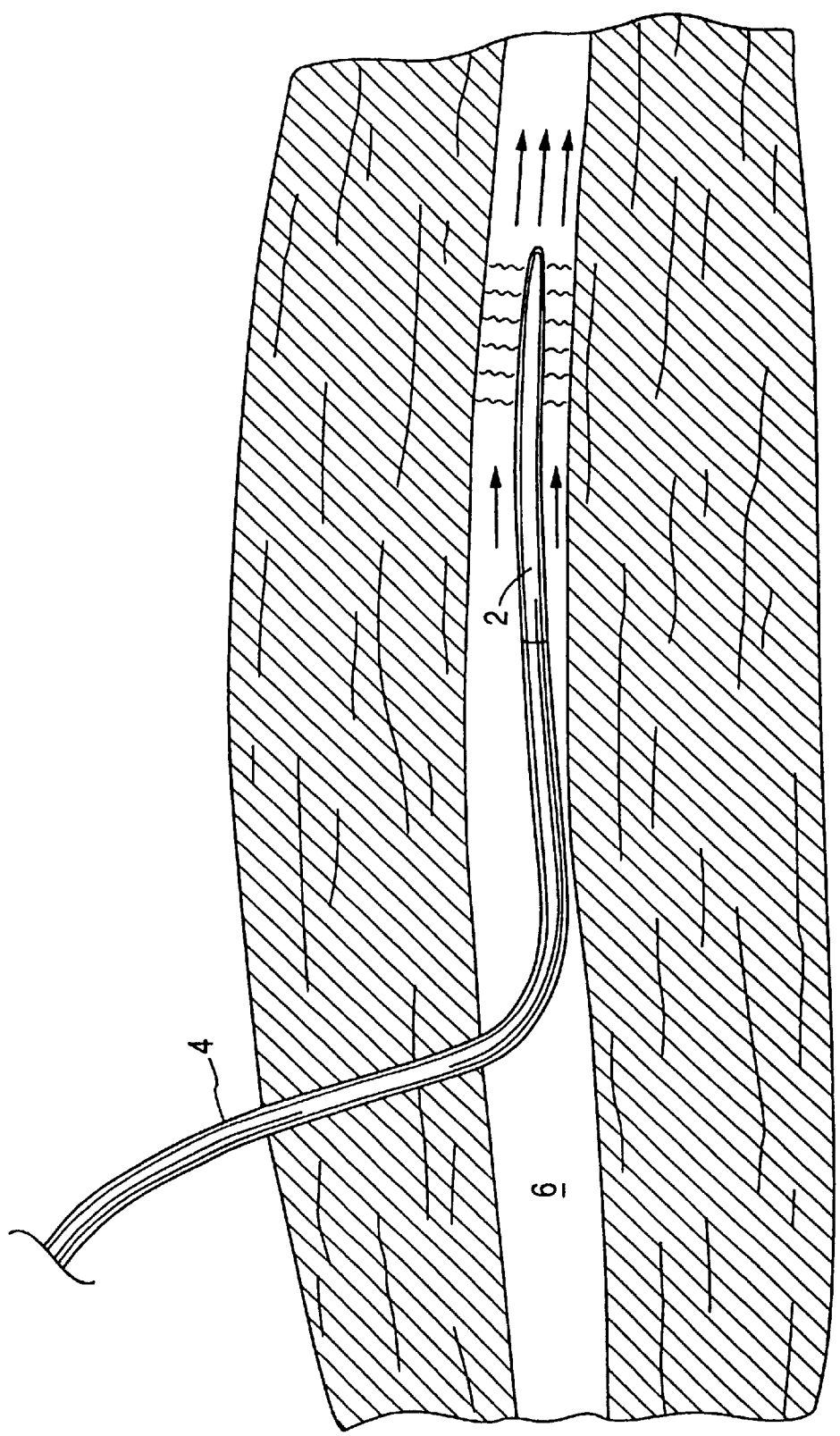
FIG. 1 depicts a heat exchange device inserted percutaneously into a blood vessel of a patient.

The present invention comprises a method of controlling a patient's body temperature to a temperature below its set point temperature, such as inducing hypothermia, while simultaneously combating thermoregulatory responses of the patient. More specifically, the invention provides for a method, apparatus, kit and composition for reducing the body's temperature below its set point temperature for an extended period of time while temporarily inactivating the shivering response.

Inactivation of the thermoregulatory mechanisms allows one to lower the body temperature below the set point temperature while reducing shivering in the patient. The methods described herein inactivate the thermoregulatory response by means of an agent selected from the group consisting of α2-adrenoreceptor agonists, non-opiod analgesic monoamine uptake inhibitors and neuropeptides, which functions as an anti-shivering mechanism, and which can be administered prior to, simultaneous with, or subsequent to initiation of the temperature lowering step.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. Additionally, when examples are given, they are intended to be exemplary only and not to be restrictive. For example, when an example is said to "include" a specific feature, that is intended to imply that it may have that feature but not that such examples are limited to those that include that feature.

The term "set point temperature" is used herein to refer to the temperature that the body attempts to maintain through the thermoregulatory responses. The set point temperature can vary both between individuals and within the same individual at different times. For example, in a healthy individual, the set point temperature is usually about 37° C. However, the set point temperature can be changed, for example when an individual is ill and the body develops a fever. In that instance the thermoregulatory system actually works to maintain a higher than normal body temperature. Thus, in such circumstances the set point temperature can be higher than 37° C.

As used herein, the term "lowered temperature state" is intended to mean a state where the temperature of all or a portion of a patient's body has been reduced to a temperature below the set point temperature. The term "lowered temperature state" includes, for example, the lowering of an elevated body temperature to normothermic (about 37° C.). Here, the set point temperature is a fever and the body temperature is reduced to 37° C., a temperature below the fevered set point temperature. More typically, the term "reduced temperature state" refers to a "hypothermic state", which can occur when the normal body temperature of 37° C. is reduced to a lower temperature, i.e., the set point temperature is a normal 37° C. state and the body temperature is reduced to below 37° C. Typically, hypothermia may be induced by lowering the patient's temperature until it is about 32° C. It is understood, however, that these temperature values provide a useful basis for discussion but definitions vary widely in the medical literature.

As used herein the term "normothermic" is intended to mean a temperature of about 37° C. (98.6° F.).

As used herein, the term "shivering" is intended to mean the uncontrolled muscle movement that an animal typically experiences when cold that does not result in controlled and coordinated movement of the organism, and includes, for example, trembling and quaking. More precisely, the term is used to mean the, trembling or quaking that an animal experiences when it's body temperature falls to a certain temperature below its set point temperature, said "certain temperature" sometimes being referred to as the "shivering threshold".

As used herein, the term "reduce" as it pertains to shivering is intended to include minimizing shivering to a noticeable degree, eliminating shivering in its entirety and preventing shivering from starting.

As used herein, the term "patient" will typically be mammalian, and most commonly a human. As such, the term "therapeutically effective amount" is intended to mean a dosage sufficient to reduce shivering in the patient being treated, and will vary depending upon various factors such as the patient species, the particular α2-adrenoreceptor agonist, non-opiod analgesic monoamine uptake inhibitor or neuropeptide used, the patient's age, weight and other characteristics, including any individual sensitivity.

In general, the method of the invention relates to controlling the temperature of all or a portion of a patient's body to a temperature below its set point temperature, while reducing shivering. One example of the method of the invention comprises the steps of: (a) sensing the temperature of all or a portion of the patient's body; (b) generating a signal based upon the sensed temperature; (c) controlling the temperature of all or a portion of the patient's body based upon the signal; and (d) administering an:agent selected from the group consisting of α2-adrenoreceptor agonists, non-opiod analgesic monoamine uptake inhibitors and neuropeptides to the patient.

As used herein, the term "controlling the temperature" is intended to include lowering the temperature below the set point temperature, raising the temperature from an initial temperature below the set point temperature, raising the temperature at a predetermined rate or increase, and maintaining the temperature at a stable temperature below the set point temperature. Such stable temperature can be, for example, normothermia.

An example of one such method comprises the steps of: (a) positioning a heat exchange device within the patient and in heat exchanging proximity to body fluid such as blood; (b) utilizing the device to lower the temperature of said body fluid to a sufficient degree and for a sufficient duration to alter the temperature of said body; and (c) administering an agent selected from the group consisting of α2-adrenoreceptor agonists, non-opiod analgesic monoamine uptake inhibitors and neuropeptides to the patient. As used herein, the term "utilize" is intended to include, for example activating the device, adjusting the thermal output of the device and deactivating the device. The positioning step can involve, for example, placing a heat exchange device having a heat exchange region into the vascular system of the patient. The temperature of the heat exchange region is then controlled for a sufficient time to affect the temperature of the patient.

Although the methods of the invention may be used to cool the entire patient's body, they may be useful in cooling a specified portion of a patient's body. For example, the methods of the invention may cool the brain or a portion thereof to deter neural damage following a stroke or other insult (e.g., period of ischemia, period of hypoxia, hemorrhage, trauma, etc.). In this manner, the heat exchange device would be positioned in a blood vessel which leads to the brain, such as the right common carotid artery, left common carotid artery, innominate artery, right internal carotid artery, left internal carotid artery, and so forth. Alternatively, the heat exchange device may be positioned in a large vein such as the inferior vena cava and heat removed from the blood for a sufficient length of time to cool the entire body and thus cool the neural tissue, such as the brain and spinal cord, as well.

It may also be desirable to cool the entire patient's body such as a febrile patient. For example, in stroke patients who have become febrile, it may be therapeutically desirable to reduce the body's temperature to normotherinic. In particular, the methods of the invention find utility in treating patients that have suffered a stroke, since stoke patients often develop a fever. Even a slight fever in these cases is correlated with much worse outcomes than in patients who do not have a fever. In such cases, it is advantageous to maintain the patient at normothermia. However, since patient's with a fever often have their set point reset to a temperature above normothermia, even reducing the patient's temperature to normal in those cases may trigger shivering with the attendant problems.

The methods of the invention serve to lower the temperature to a temperature below its set point temperature, while simultaneously inactivating the thermoregulatory response by means of an anti-shivering mechanism. The order of the steps of the method can be conducted several ways in that the α2-adrenoreceptor agonist, non-opiod analgesic monoamine uptake inhibitor or neuropeptide can be administered prior to, simultaneous with, or subsequent to initiation of the temperature lowering step. In this manner, the α2-adrenoreceptor agonist, non-opiod analgesic monoamine uptake inhibitor or neuropeptide can be administered to the patient: prior to controlling the body temperature, for example, prior to positioning a heat exchange device; after positioning the device but before utilization; simultaneous with the utilization step (b); or subsequent to the utilization step.

Figure 23:
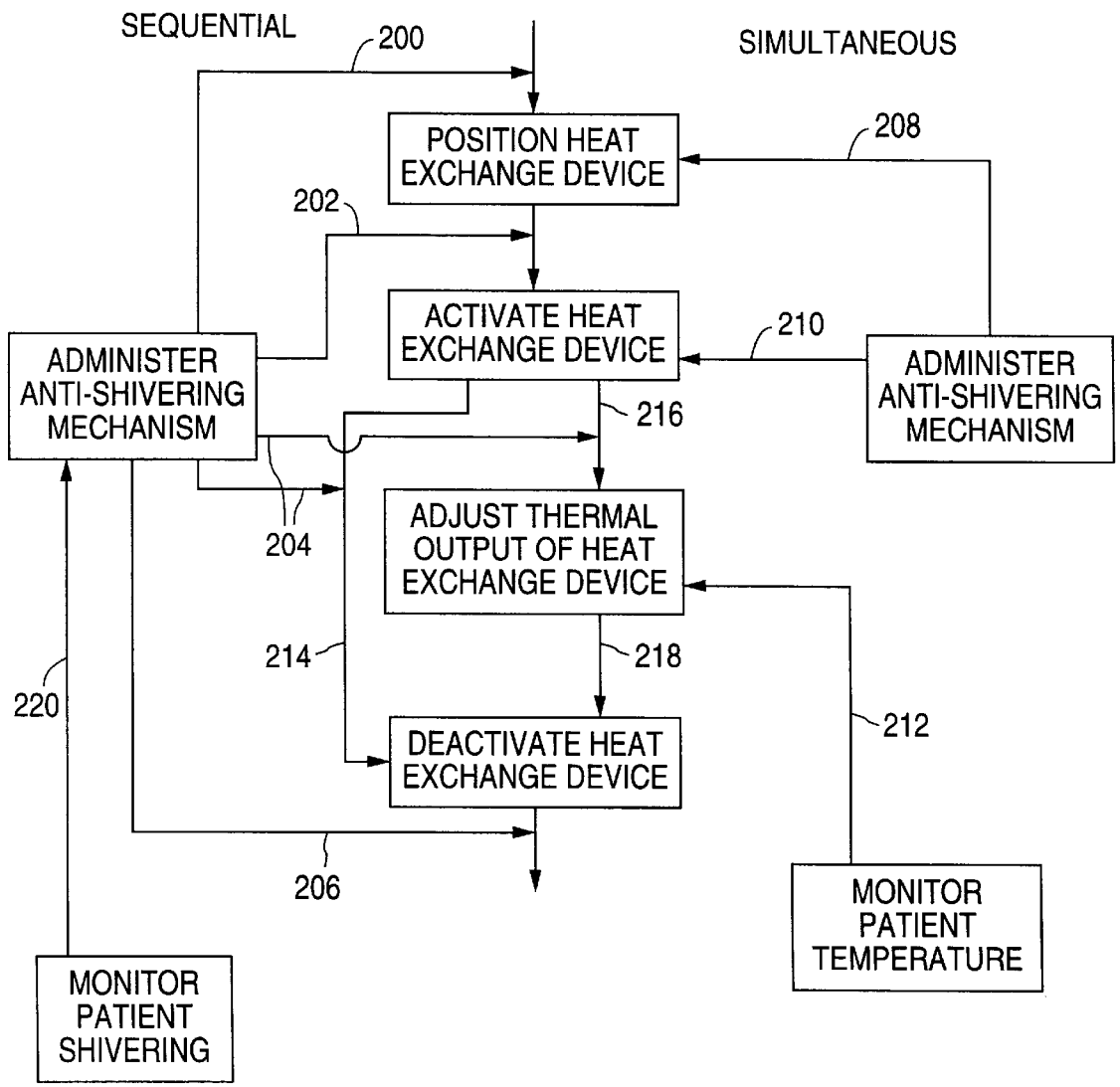
FIG. 23 is a flow chart illustrating a preferred method of the invention.

Several acceptable methods are illustrated in FIG. 23 in the form of a flow chart. For sequential administration routes, the α2-adrenoreceptor agonist, non-opiod analgesic monoamine uptake inhibitor or neuropeptide can be administered before positioning the heat exchange device (200), after the device has been positioned (202), after the device has been activated (204), or after the device has been deactivated (206), the latter being useful if it is desired to administer the anti-shivering mechanism after the body has already been cooled to the desired temperature. For simultaneous administration routes, the α2-adrenoreceptor agonist, non-opiod analgesic monoamine uptake inhibitor or neuropeptide can be administered simultaneously with the positioning of the heat exchange device (208) or while the device is activated (210). The invention also contemplates administering the α2-adrenoreceptor agonist, non-opiod analgesic monoamine uptake inhibitor or neuropeptide in any combination of the aforementioned sequential and simultaneous routes.

In another aspect of the invention, a method of controlling the temperature of a patient below the set point temperature comprises the steps of: (a) employing internal in vivo core temperature regulation; and (b) administration of an agent selected from the group consisting of α2-adrenoreceptor agonists, non-opiod analgesic monoamine uptake inhibitors and neuropeptides. One means of employing internal in vivo core temperature regulation comprises placing a heat exchange device in the blood vessels of the patient, where the heat exchange device has a heat exchange region that is in contact with the flowing blood of the patient. The temperature of the heat exchange region can then be controlled for a sufficient time to affect the temperature of the patient. The heat exchange device may be a catheter having a shaft for the circulation of heat exchange fluid therein. The heat exchange region can be a balloon; and the temperature of the heat exchange region is controlled by circulation of heat exchange fluid through the shaft and the interior of said balloon.

As noted above, the cooling aspect of the invention operates to cool the entire patient's body to lower the patient's body temperature, or to cool a portion of the patient's body, for example, to minimize damage to a particular body tissue.

In a preferred method of the invention, the body temperature is lowered by cooling a body fluid in situ for a sufficient length of time to lower the temperature by the desired amount, while reducing patient shivering that typically accompanies such cooling by administering an α2-adrenoreceptor agonist, non-opiod analgesic monoamine uptake inhibitor or neuropeptide. Typical body fluids include, blood, cerebral spinal fluid, peritoneal fluid or the like, but will typically be blood. In addition, the methods of the invention will generally result in in situ cooling of target body tissues and organs, either by cooling body fluid directed to the tissue, as in cooling the brain by cooling blood flowing through the carotid artery, or by cooling the whole body which results in cooling the target tissue. Typical body tissues and organs that may be the target tissue include, neural tissue, brain, heart, spinal cord tissue, kidney, liver and the like, but will typically be the heart and the brain.

The heat exchange device itself may have a temperature within the range of 0 to 42° C. By controlling the temperature of the portion of the device that is in heat exchanging proximity to the body fluid so that a temperature differential (ΔT) exists between the heat exchange device and the body fluid, heat is transferred between the device and the body fluid. For example, when the body temperature is lowered by cooling blood, the heat exchange device is positioned within a blood vessel and maintained with a temperature below that of the blood flowing past the heat exchange device so that heat is transferred between the device and blood flowing through the vessel. Blood flows in heat transfer proximity to the heat exchange device and is cooled. By continuing to cool fluid flowing past the heat exchanger in sufficient volume and for a sufficient length of time, the temperature of the patient is reduced. The methods of the invention are suited to lower the body temperature of a patient by as much as 9° C. It is not expected to reduce the patient's body temperature to less than 28° C., and preferably not lower than 32° C.

Another important aspect of the instant invention is that the temperature of the patient's body or portion thereof can be reduced controllably, thus avoiding the problems associated with cooling a patient too rapidly, or below a desired temperature. Likewise, when a hypothermic patient is warmed, the combination of an internal heat exchange device controlled by feedback with the anti-shivering agent that reduces the body's shivering and thus allow more precise control over the patient's temperature, permits a more gradual and gentle warming of the patient. It will be readily seen that if a patient is maintained at a reduced temperature below the set point temperature and particularly below the shivering threshold, the administration of the anti-shivering agent in combination with feed-back controlled in vivo heat exchange permits a more effective temperature control of the patient. In particular, when inducing hypothermia, a target tissue can be cooled to the desired temperature and that temperature maintained by controlling the heat exchange device. This is shown schematically in FIG. 23, where feedback information is obtained from the patient, for example, the patient's temperature is measured (either the temperature of the entire body, the target tissue or fluid), and that feedback information is used in a feedback system (212) to continually control or adjust the output of the heat exchange device. In this manner, the feedback system may be used to achieve or maintain, for example a predetermined body or body fluid temperature, a predetermined heat exchange device temperature or a predetermined ΔT. This is optional, however. The methods of the invention are well suited for use where the device may operate in a simple on-off mode. That is, it may operate at full power until deactivated (214) or where the device is activated, adjusted one or more times during its operation (216) and then deactivated (218). Feedback information can also be obtained from the patient regarding the amount of shivering being experienced and this feedback system (220) can be used to continually control or adjust the administration of the anti-shivering agent.

Generally the methods of the invention will involve affecting the temperature of the entire body, but different regions may be controllably maintained at temperatures different from each other, for example, by controlling different heat exchange devices at different locations with the patient's body.

In one embodiment of the invention, the heat exchange device is positioned within the patient, preferably intravascularly. For example, the heat exchange device, such as a catheter, is inserted through a puncture or incision into a fluid containing portion of the patient's body, for example, percutaneously into a blood vessel. An internally positioned device, i.e., core cooling, is advantageous as it circumvents vasoconstriction. Accordingly, in one embodiment of the invention, a method of controlling a mammalian patient's temperature below the patient's set point temperature, while inhibiting the patient's thermoregulatory responses, comprises the steps of (a) positioning a heat exchange device in a blood vessel, for example a blood vessel leading to the vena cava or brain; (b) utilizing the device to decrease the temperature of blood which passes in heat exchanging proximity to the heat exchange device; and (c) administering an agent selected from the group consisting of α2-adrenoreceptor agonists, non-opiod analgesic monoamine uptake inhibitors and neuropeptides to the patient.

The heat exchange device can have the configuration of a number of medical devices that are well known in the art. Although a catheter is preferred, it is understood that any other suitable means of cooling the body and/or target fluid or tissue is suitable for use in the instant invention, and that the particular catheter configurations described herein are intended to be exemplary and not limiting in any manner. The preferred heat exchange mechanism involves heat exchanger in contact with a body fluid or tissue on its external surface, the heat exchanger being chilled or heated on its internal surface by circulation of a chilled fluid which is preferably sterile saline or other biocompatible fluid having appropriate heat transfer characteristics.

In one embodiment of the invention, a method of controlling a patient's temperature comprises utilizing a heat exchange device which is a catheter. In addition, an anti-shivering agent is administered to the patient to reduce shivering. A suitable catheter comprises an elongate flexible catheter having a heat exchanger which is capable of exchanging heat between blood or other body fluid which flow in heat exchanging proximity thereto. For example, a catheter having a heat exchanger or heat exchange region which may be, for example, a balloon with fins, is inserted through a puncture or incision into a fluid containing portion of the patients body, for example, a blood vessel. The temperature of the balloon is controlled by the circulation of a heat exchange fluid through the interior of the balloon. Blood flows in heat transfer proximity past the heat exchanger. Heat exchange proximity requires sufficient proximity for effective heat exchange to occur and depends on such factors as the chemical and physical make-up of the blood, the rate of flow past the heat exchange surface, the pattern of blood flow past the heat exchanger, (laminar flow, turbulent flow, and the like), the difference in temperature between the heat exchange surface and the blood, the material of which the heat exchange surface is made, and the proximity between the heat exchange surface and the blood. By continuing to cool fluid flowing in heat transfer proximity for a sufficient length of time, the body temperature of the patient is altered.

Anti-shivering Mechanism

As used herein, the term "anti-shivering mechanism" is intended to mean the administration of an anti-shivering agent selected from the group consisting of α2-adrenoreceptor agonists, non-opiod analgesic monoamine uptake inhibitors and neuropeptides to a patient.

As used herein, the terms "α2-adrenoreceptor agonist", "non-opiod analgesic monoamine uptake inhibitor" and "neuropeptide" are intended to mean any biologically active agent or drug or combination of agents or drugs within that class, that is administered to a patient for the purpose of reducing shivering. The term is also intended to include pharmaceutically acceptable salts or variants of such agents which retain the biological effectiveness of the agents themselves. Such salts are often preferred as the salt form may have better solubility, increased duration of action, and so forth. Suitable salts are well known to those of skill in the art and may include the hydrochloride, methanesulfonate, mesylate, maleate, decanoate, enanthate, succinate, lactate, sulfate, and quaternary ammonium salts.

The α2-adrenoreceptor agonists suitable for use in the methods of the invention, include by way of illustration and not limitation, dexmedetomidine; detomidine; medetomidine; clonidine; bromonidine; tizanidine; mivazerol; guanfacine; oxymetazonline; (R)-(−)-3'-(2-amino-1-hydroxyethyl)-4'-fluoro-methanesulfoanilide; 2-[(5-methylbenz-1-ox-4-azin-6-yl)imino]imidazoline; 5-bromo-N-(4,5-dihydro-1H-imidazol-2-yl)-6-quinoxalinamine; 5,6,7,8-tetrahydro-6-(2-propenyl)-4H-thiazolo[4,5-d]azepin-2-amine; 6-ethyl-5,6,7,8-tetrahydro-4H-oxaazolo[4,5-d]azepin-2-amine; 5,6-dihydroxyl-1,2,3,4-tetrahydro-1-naphyl-imidazoline; and pharmaceutically acceptable salts thereof.

The non-opiod analgesic monoamine uptake inhibitors suitable for use in the methods of the invention, include by way of illustration and not limitation, nepofam; tramadol; and pharmaceutically acceptable salts thereof.

The neuropeptides suitable for use in the methods of the invention, include by way of illustration and not limitation, neurotensin; neurotensin analogs; bombesin; neuromedin; dermorphin; D-ala-deltorphin; and pharmaceutically acceptable variants thereof.

In most cases, however, when administered alone, a high dosage may be required to achieve a desired temperature drop. In the instant invention, the reduced temperature state is induced by a heat exchange device, such as a cooling catheter, while the anti-shivering agent is used to overcome shivering. Several agents from different classes may also be administered in combination, for example an α2-adrenoreceptor agonist may be administered in combination with a neuropeptide. In this manner, small non-toxic dosages can be administered to achieve the desired anti-shivering results. Accordingly, the suitability of an anti-shivering agent for use in the methods described herein depends upon its ability to suppress the thermoregulatory mechanisms to reduce shivering during cooling and thereafter while the patient is maintained at a temperature that would otherwise produce shivering.

As noted above, pharmaceutically acceptable salts of the $\alpha_2$-adrenoreceptor agonist are also well suited for use in the methods of the invention. These include dexmedetomidine hydrochloride, and so forth. Pharmaceutically acceptable salts of the non-opiod analgesic monoamine uptake inhibitors are also well suited for use in the methods of the invention as are pharmaceutically acceptable variants of the neuropeptides.

Typically, the anti-shivering agent or pharmaceutically acceptable salt or variant thereof will be administered in combination with a pharmaceutically acceptable carrier.

A particularly well-suited α2-adrenoreceptor agonist is dexmedetomidine and its salt, dexmedetomidine hydrochloride (sold by Abbott Laboratories under the mark Precedx™). Exposure to temperature extremes is often associated with increases in circulating catecholamine concentrations. Dexmedetomidine is of particular interest since it acts as an anti-shivering agent, as well as acting to counter the surge in catecholamine levels that can occur when a patient's body temperature drops below its set point temperature. In addition, dexmedetomidine, as well as nepofam and neurotensin, causes minimal depression of the respiratory drive in patients, as opposed to other agents such as opiods.

Dosage of Anti-shivering Agents

A therapeutically effective amount of the anti-shivering agent selected from the group consisting of α2-adrenoreceptor agonists, non-opiod analgesic monoamine uptake inhibitors and neuropeptides is to be administered, which is intended to be a dosage sufficient to reduce or eliminate shivering in the patient being treated. The actual dosage amount will vary depending upon the patient's age and weight, along with the dosage form and α2-adrenoreceptor agonist, non-opiod analgesic monoamine uptake inhibitor or neuropeptide selected. Generally a typical dosage will be within the range of about 0.5 to 10 mg/kg of body weight, preferably about 0.5 to 2.0 mg/kg of body weight, and most preferably about 0.5 to 1.0 mg/kg of body weight. It is believed that 0.1 mg to 5.0 g of the anti-shivering agent will provide a therapeutic effect in the methods of the invention.

The preferred dosage will be dependent upon the time period during which the patient's body temperature is being reduced (either from a fevered state to normothermic or from normothermic to a hypothermic state), along with the actual drop in patient temperature that will be experienced during this procedure. Accordingly, for the methods of the instant invention, the amount of anti-shivering agent administered should be sufficient to reduce shivering while the body temperature is being reduced and maintained at the lower temperature, which may be 24–72 hours.

It is important to note that the amount of anti-shivering agent required for maintaining a patient at a predetermined temperature without shivering may be different than the amount required when the patient's temperature is being lowered to reach a predetermined temperature. For example, a patient may require a different dose of an anti-shivering agent, generally more, to prevent shivering during active cooling than the dose needed to prevent shivering while being maintained at the target temperature. For this reason, it may be desirable to monitor the level of patient shivering, as shown in FIG. 23, so that the administration of the anti-shivering agent can be adjusted accordingly. Another factor to consider when selecting a dosage is the rate at which the temperature of the patient is being changed, i.e. the rate of cooling, since this may affect the shivering response and thus the dose of anti-shivering agent that is appropriate. Likewise, the shivering response may be different at different temperatures below the shivering threshold. For example, a patient might shiver more vigorously at 34° C. than at 32° C. Additionally, of course, individuals will vary widely in their shivering thresholds, the vigor of their shivering response, and their sensitivity to the agent. The various α2-adrenoreceptor agonists, non-opiod analgesic monoamine uptake inhibitors and neuropeptide may also vary in strength depending on their individual purity and preparation. For all these reasons, dosage recommendations herein are merely suggestive and by no means comprehensive or restrictive.

Route of Administration of Anti-shivering Agents

There are numerous routes and formulations by which the α2-adrenoreceptor agonist, non-opiod analgesic monoamine uptake inhibitor or neuropeptide can be administered to the patient undergoing the hypothermia inducing procedures described herein. For example, the anti-shivering agent can be administered either alone or in combination with other pharmaceutically acceptable excipients, including solid, semi-solid, liquid or aerosol dosage forms, such as, for example, tablets, capsules, powders, liquids, injectables, suspensions, suppositories, aerosols or the like. The anti-shivering agent can also be administered in sustained or controlled release dosage forms, including depot injections, osmotic pumps, pills, transdermal (including-electrotransport) patches, and the like, for the prolonged administration of the anti-shivering agent at a predetermined rate. The compositions will typically include a conventional pharmaceutically acceptable carrier or excipient and the anti-shivering agent or a pharmaceutically acceptable salt thereof. In addition, the composition may include other medicinal agents, pharmaceutical agents, carriers, adjuvants, and so forth. Generally, depending on the intended mode of administration, the pharmaceutically acceptable composition will contain about 0.1–90.0% by weight, preferably about 0.5–50.0 wt %, of the anti-shivering agent or its salt, the remainder being suitable pharmaceutical excipients, carriers, etc. See, for example, "Remington's Pharmaceutical Sciences" (Mack Publishing Company, Pennsylvania, 18th Edition, 1990) and "Goodman & Gilman's the Pharmacological Basis of Therapeutics", (Goodman, et al., Eds., 9th edition, 1996) for extensive discussions on the preparation and composition of various formulations suitable for use in administering the anti-shivering agents described herein.

The anti-shivering agent can be administered orally, transdermally, directly into the cerebrospinal fluid (e.g., intraceroboventricualrly or intracisternally) or parenterally (intramuscularly or intravenously), with intramuscular or intravenous injection being the preferred routes of administration.

For oral administration, the compositions may take the form of a solution, suspension, tablet, capsule, powder, sustained release formulation and the like. A typical pharmaceutically acceptable composition is formed by the incorporation of any of the normally employed excipients, such as, for example, a diluent (lactose, sucrose, glucose, dicalcium phosphate), lubricant (magnesium stearate), disintegrant (croscarmellose sodium), binder (starch, gum acacia, polyvinylpyrrolidone, gelatin, cellulose, cellulose derivatives), mannitol, povidone, sodium saccharine, talcum, magnesium carbonate, and the like. Such compositions take the form of solutions, suspensions, tablets, dispersible tablets, pills, capsules, powders, sustained release formulations and the like.

Liquid pharmaceutically administrable compositions can, for example, be prepared by dissolving or dispersing an anti-shivering agent and optional pharmaceutical adjuvants in a carrier, such as, for example, water, saline, aqueous dextrose, glycerol, glycols, ethanol, and the like, to thereby form a solution or suspension. If desired, the pharmaceutical composition may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, triethanolamine oleate, etc. Liquid or semi-solid oral formulations can also be prepared by dissolving or dispersing the anti-shivering agent or its salt in vegetable oils, glycols, triglycerides, propylene glycol esters (e.g. propylene carbonate) and the like, and encapsulating these solutions or suspensions in hard or soft gelatin capsule shells to provide a solid dosage form.

Formulations for parenteral injection can be prepared in conventional forms, either as liquid 'solutions or suspensions, solid forms suitable for solution or suspension in liquid prior to injection, or as emulsions. Formulations of 0.1 to 10 wt % anti-shivering agent in solution are acceptable, with 2.5 wt % being typical.

Timing of Administration of the Anti-shivering Agent

When inducing hypothermia, it is preferred to have therapeutic levels of the α2-adrenoreceptor agonist, non-opiod analgesic monoamine uptake inhibitor or neuropeptide anti-shivering agent in the blood stream or maintenance of the skin temperature already established by warming the skin, while the heat exchange device is being used to lower the patient's core temperature. Accordingly, the preferred methods of the invention contemplate administration of the anti-shivering agent prior to initiation of the cooling step. When controlling the rate of heating of an already hypothermic patient, or when maintaining hypothermia at a stable temperature below the shivering threshold, it is also preferable to have therapeutic levels of the anti-shivering agent in the blood stream or the skin temperature already being maintained by warming the skin. This can be accomplished by administering a bolus dosage to achieve the desired therapeutic level of anti-shivering agent in the blood, which can then be subsequently maintained by periodic or continuous administering the anti-shivering agent. The anti-shivering agent may be administered periodically at a larger dose, for example intramuscular, or can be administered continuously at a smaller dose, for example intravenously.

The anti-shivering agent may be administered prior to positioning the heat exchange device, before the cooling step commences, simultaneous with the cooling step, which can commence at the time the device is inserted or applied externall to the patient or at the time that the heat exchange device is activated, or at a point in time subsequent to the initiation of the cooling step. Yet another embodiment contemplates continuing to administer the anti-shivering agent for some time after the heat exchange device has ceased to operate. As noted above, a single one-time dosage of agent, several periodic dosages of agent administered at set time intervals, continuous administration of agent, or a combination of these are also contemplated. The actual timing of administration of the anti-shivering agent is best illustrated in FIG. 23, which shows the numerous points at which the anti-shlivering agent can be administered, either sequentially or simultaneously with the other steps in the methods of the invention.

Heat Exchange Devices

The heat exchange device itself is preferably a catheter which comprises at least one fluid lumen through which a thermal exchange fluid may be circulated, a heat exchanger and a working lumen extending from outside the patient through at least part of the catheter that is inserted into the patient. An example of such a catheter may be an elongate catheter having a proximal end and a distal end, where the entire length of said flexible catheter is defined as the distance from its proximal end to its distal end and comprising at least one fluid lumen through which a thermal exchange fluid may be circulated, a heat exchanger with heat exchange fins located at a first location on the catheter, and a working lumen extending from outside the patient through at least part of the catheter that is inserted into the patient.

The heat exchanger operates to exchange heat between blood which flows in heat exchanging proximity to the heat exchanger and a thermal exchange fluid which is circulated through the catheter. The first location at which the heat exchanger is located may constitute less than the entire length of the catheter, and is typically at or near the distal end of the catheter. The heat exchanger may specifically comprise a balloon or other structure through which the thermal exchange fluid may circulate, and the heat exchange fins may be a plurality of lobes of the balloon or other surface area increasing projections such as outwardly extending protuberances, ribs, filaments of a multi-filament device, curved or undulating surfaces, etc., that enhance the efficiency with which heat exchange occurs.

The inventions also contemplates a means for controlling the heat exchange device so that a predetermined temperature is established and maintained. For example, a control system can monitor body temperature and the device is then controlled in response to the body temperature. In this manner, the device can be modulated or shut off when the patient's body or target region reaches a pre-selected temperature, and similarly, can be modulated, for example turned on, when the temperature deviates from the pre-selected temperature.

Figure 24:
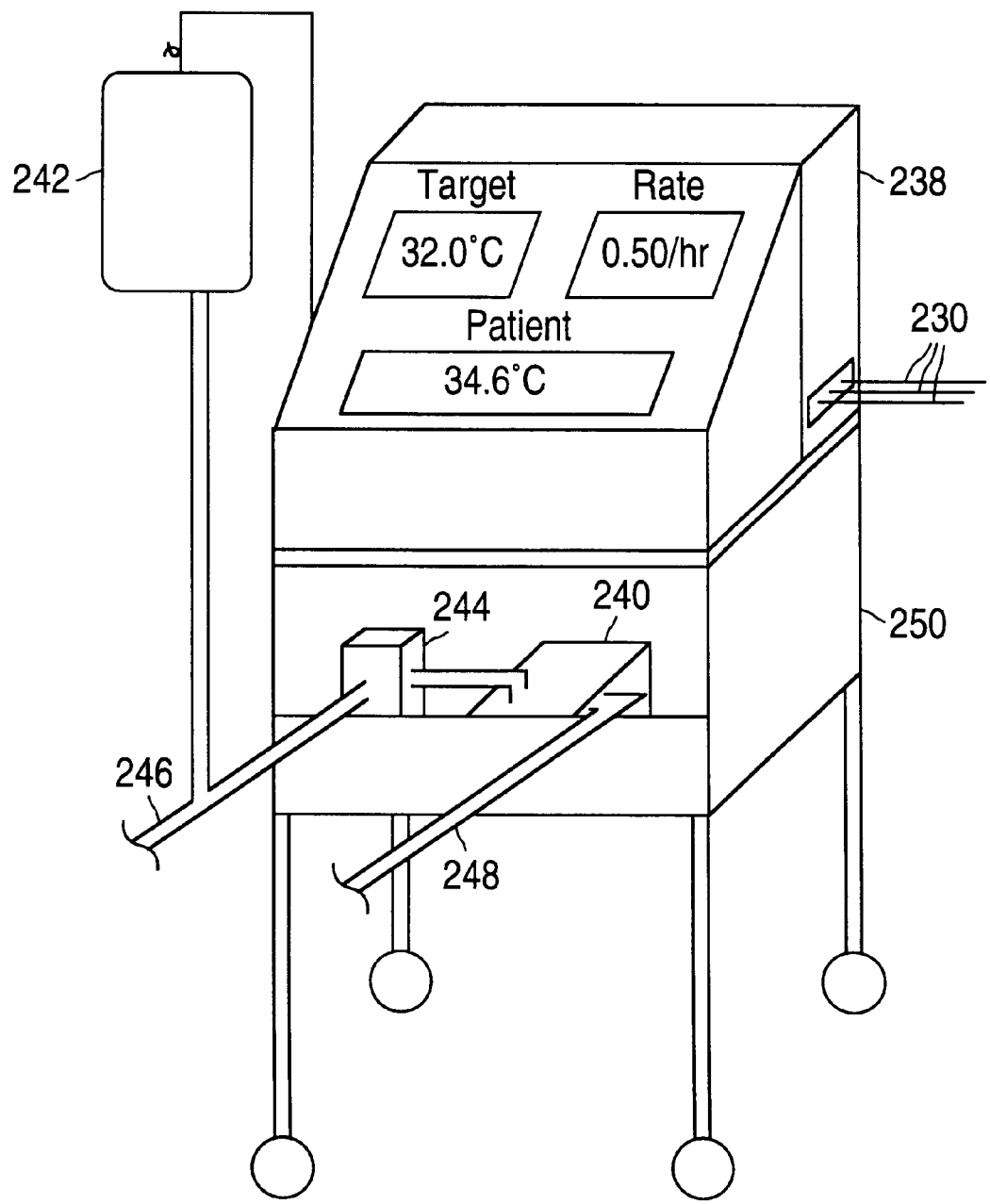
FIG. 24 is a front view of control system useful in the methods of the invention.
Figure 25:
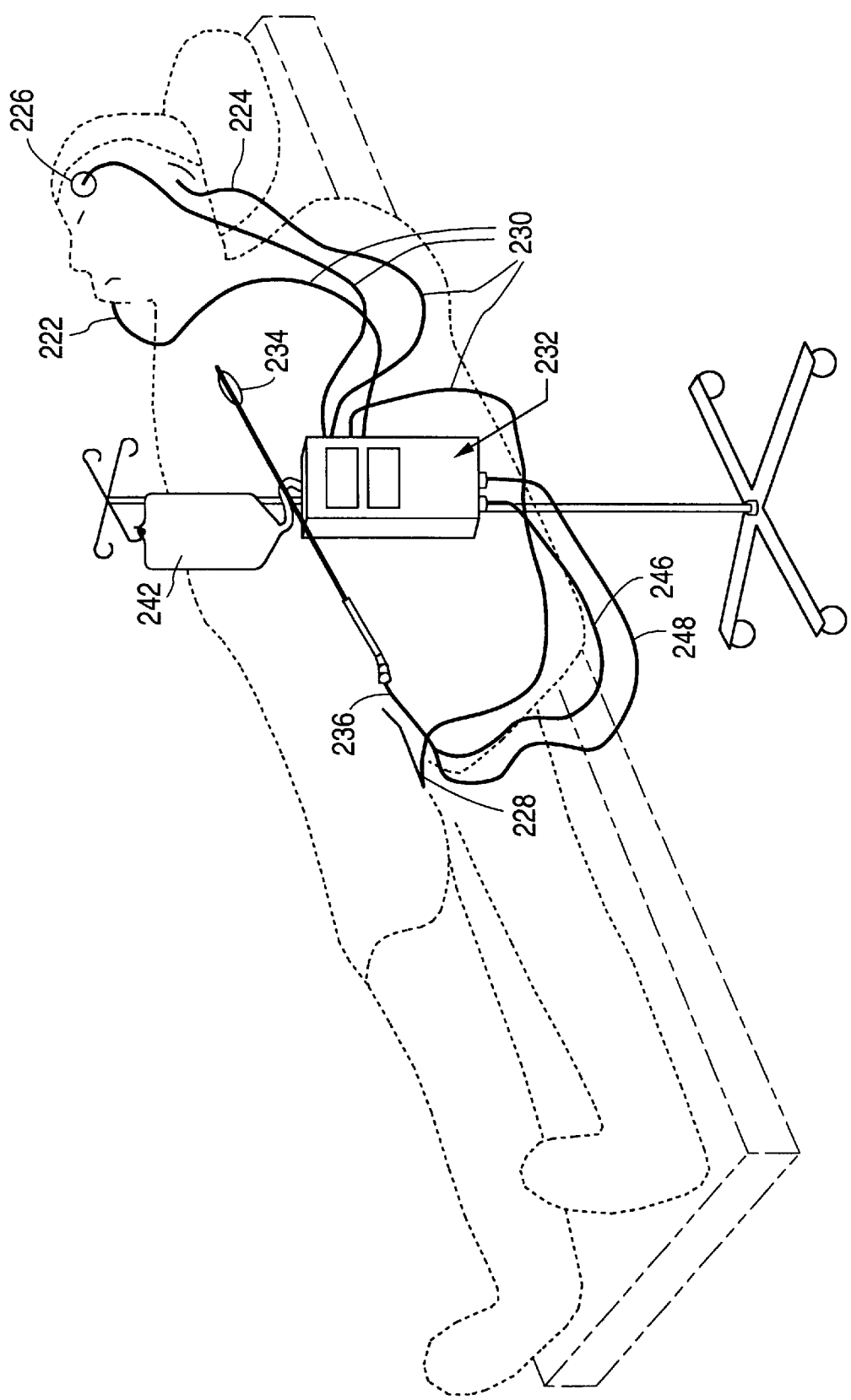
FIG. 25 illustrates a control system in operation.

A significantly more sophisticated and automatic control over temperature regulation is possible. Examples of such control systems are shown in FIG. 24 and FIG. 25. In the control system, feedback from the patient's body is obtained by one or more temperature sensors attached to the patient. Examples include an esophageal temperature probe 222, a tympanic temperature probe 224, a skin temperature probe 226, a rectal temperature probe 228, or other appropriate sensors as is well known in the art. These probes generate signals that represent the temperature sensed and transmit those signals over a plurality of wires 230 to a control unit 232, one embodiment of which is illustrated in FIG. 25. The control unit receives the temperature signals and controls the heat exchange region 234 of the heat exchange catheter 236 in response thereto.

FIG. 25 illustrates another embodiment of a control unit 250 may include a programmable computer 238, a thermoelectric heater/cooler 240, a supply of heat exchange fluid 242, and a pump 244. The pump may pump the heat exchange fluid through the supply source, for example, a bag 242 over the thermoelectric heater/cooler to alter the temperature in the fluid. The fluid may be pumped from an inlet tube 246 received from the heat exchange catheter, through the bag and back to the heat exchange catheter through the outlet tube 248. In response to the temperature sensed, the controller may control the pump rate, or may control the temperature of the thermoelectric heater/cooler.

In one embodiment, the control unit is programmed to control the heat exchange catheter to reach and maintain a target temperature. The supply of heat exchange fluid is a closed loop of heat exchange fluid circulating through the catheter inside the patient and external of the patient through the bag of fluid positioned adjacent the thermoelectric heater/cooler. As the sensed temperature of the patient approaches the target temperature, the control unit may adjust the temperature of the thermoelectric heater/cooler to approach the target temperature. For example, if the computer was programmed to control the patient's temperature at 32° C., the thermoelectric cooler might originally be at a temperature of near 0° C., and thus the temperature of the heat exchange fluid flowing within the balloon would be about 0° C. However, as the temperature of the patient fell and began to approach 32° C., the control unit would act to increase the temperature of the thermoelectric heater/cooler (by altering the current flowing therethrough, for example) so that it began to warm toward 32° C. It has been found that a temperature of the heat exchange fluid of about 30° C. will remove approximately the amount of heat that a body at rest at 32° C. generates, so as the body temperature reaches the target temperature of 32° C., the control unit will gradually control the thermoelectric heater/cooler to level off at a constant temperature of 30° C.

Similarly, the control unit may regulate the rate of temperature change. A rate of change of patient temperature may be programmed into the computer of the controller. If the sensed temperature of the patient is changing more rapidly or more slowly than the programmed rate, the temperature of the heat exchange fluid may be controlled by controlling the thermoelectric heater/cooler and thus removing or adding heat through the heat exchange catheter to the blood of the patient in appropriate amounts to control the rate of temperature change in the patient.

It may be readily seen that many variations on this control unit are possible without departing from the invention. For example, the control unit may receive signals from one, two or more temperature sensors, which would be included in the control system. Sensors of other parameters than body temperature, such as pulse rate or blood pressure or the like, are within the contemplation of the invention, and may also be included in the control system. Likewise, the target temperature is only one end point that may be desirable with the controller; the target may be some other bodily condition such as blood pressure, EEG condition, and the like. Also the nature of the response of the control unit which serves to control the heat exchanger may vary. It may be a simple as an on/off response. It may vary the rate of pumping, the temperature of the thermoelectric plate, or any other suitable variable to control the heat Kits Another aspect of the invention pertains to a kit for reducing the temperature of a patient comprising (a) a heat exchange device and (b) an agent selected from the group consisting of α2-adrenoreceptor agonists, non-opiod analgesic monoamine uptake inhibitors and neuropeptides. The kit may contain instructions, as appropriate, both as to the operation of the device and the anti-shivering mechanism.

The kit may also include information pertaining to the storage and dosage instructions for the agent, and so forth For example, the kit may contain instructions for the proper insertion oft he catheter into the vascular system as is well known in the medical arts, for example by the Seldinger technique. The instructions may also contain a description of the proper use of the heat exchange catheter system, the proper target temperature for the patient, and if the kit contains a control unit, the appropriate ramp rates for heating and cooling the patient, as well as specific recommendations for the use of the α2-adrenoreceptor agonist, non-opiod analgesic monoamine uptake inhibitor or neuropeptide. The kit may or may not contain the anti-shivering, but may contain a description of the preferred α2-adrenoreceptor agonist, non-opiod analgesic monoamine uptake inhibitor or neuropeptide, for example a preferred α2-adrenoreceptor agonist, non-opiod analgesic monoamine uptake inhibitor or neuropeptide selected from those set out above, and suggestions as to dosage and methods of administration and the like. The duration of administration of cooling and use of the anti-shivering mechanism may also be set out.

In one embodiment of the kit, the heat exchange device is a catheter. A suitable catheter is an elongate catheter having a proximal end and a distal end, the entire length of the catheter being defined as the distance from its proximal end to its distal end, and comprises (i) at least one fluid lumen through which a thermal exchange fluid may be circulated; (ii) a heat exchanger with heat exchange fins located at a first location on the catheter; and (iii) a working lumen extending from outside the patient through at least part of the catheter that is inserted into the patient.

The kit can optionally include a control system that monitors body conditions, for example by measuring temperature, and controls the heat exchange device in response to the body conditions being monitored, such as turning off the device when the patient's body or target region reaches a pre-selected temperature, or reactivating the device when the temperature deviates from the pre-selected temperature. In addition, the kit may also comprise a second heat exchange device. This second device may serve to compliment the temperature lowering ability of the first device, i.e., the second device may also serve to lower the temperature of the body or portion thereof. Alternately, the second device may serve to increase the temperature of the patient's body or body portion. This is useful to provide heat in the event that the method Of the invention results in a lower temperature than is desired, or if it is desired to conclude the therapy and raise the patient's temperature to normothermic.

These and other methods of the invention are readily understood in references to the figures described below. One embodiment of the heat exchange device suited for use in the methods of the invention is illustrated in FIG. 1, which shows the distal end 2 of a heat exchange device 4, which has been inserted through the patient's skin into a blood vessel 6. Blood flow through the vessel is indicated by a set of flow arrows. Preferably, the device is inserted into a relatively large blood vessel, e.g., the inferior or superior vena cava, a femoral artery or vein, a jugular artery or vein, or the aorta. Use of these vessels is advantageous in that they are readily accessible, provide safe and convenient insertion sites, and have relatively large volumes of blood flowing through them. In general, large blood flow rates facilitate more efficient heat transfer between the catheter and the blood. For example, the jugular vein may have a diameter of about 22 French, or a bit more than 7 mm, where 1 French is 0.013 inches or 0.33 mm. A heat exchange device suitable for insertion into a vessel of this size can be made quite large relative to devices intended for insertion into smaller vessels in the vascular system.

A particularly well suited heat exchange device is a catheter. Atherectomy or balloon angioplasty catheters, used to clear blockages from the coronary artery and similar vessels, commonly have external diameters in the range between 2 to 8 French. In contrast, it is anticipated that a catheter useful in the methods of the instant invention will typically have an external diameter of about 9 French, although this dimension may obviously be varied a great deal without departing from the basic principles of the claimed invention. It is desirable that the catheter or other heat exchange device be small enough so that the puncture site can be entered using the percutaneous Seldinger technique, a technique well known to medical practitioners. Other techniques for inserting devices into the above mentioned blood vessels are also well known among medical personnel.

Although a small diameter is chosen for the heat exchange device, this diameter is based upon the pre-insertion size, and is aimed at avoiding or minimizing vessel trauma. However, after the device is inserted in the vessel, its distal end can be expanded to any size so long as blood flow is not unduly impeded. Additionally, the femoral artery and vein and the jugular vein are all relatively long and straight blood vessels. This will allow for the convenient insertion of a device having a temperature controlled region of considerable length. This is of course advantageous in that more heat may be exchanged at a given temperature for a device of a given diameter if the length of the heat transfer region is increased. Although the method of the present invention will probably be most commonly employed in a hospital, the procedure need not be performed in an operating room. The method and apparatus are so simple that the device may be inserted and treatment to lower the patient's temperature and reduce shivering may begin even in an ambulance or in the field.

In general, the distal end 2 of the device may be cooled and maintained at a temperature below the patient's body temperature. Blood flowing through the vessel will therefore be cooled, and will then be circulated rapidly throughout the patient's circulatory system. The beneficial effect of cooling the patient's blood in the vicinity of the device will thereby be spread very quickly throughout the entire body of the patient.

The device depicted in FIG. 1 can utilize a variety of cooling methods and can have numerous configurations that maximize its heat exchanging capability. A particularly well suited heat exchange device is a catheter, several configurations of which are described in detail in Ginsburg, U.S. Pat. No. 5,486,208 and Ginsburg, WO 98/26831, the disclosures of which are incorporated herein by reference. For example the catheter can have a thermally conductive shaft running the length of the catheter body, made of a metal or other material having a high thermal conductivity. By cooling the proximal end of the shaft with an external cooling apparatus, heat will be caused to flow either into the distal end of the shaft. Another cooling mechanism is provided by a catheter having two lumens running through it. Fluid flows from the proximal end of the catheter through in-flow lumen, through a heat transfer region, and back out through an out-flow lumen. By supplying cooled fluid through the inflow lumen, heat may be transferred from the patient's blood stream. Other embodiments and modifications for heat transfer other than by use of a heat exchanging fluid, e.g., resistance, including radio frequency, will occur to those skilled in the art.

The heat exchange devices useful in the methods of the invention are preferably designed to optimize the rate of heat transfer between the device and the body, tissue or fluid, for example with blood flowing through the vessel. While a large surface area is desirable in order to increasing the effective heat transfer, care must be taken so that the device does not unduly restrict blood flow through the vessel. The device can be fitted with a plurality of protrusions to maximize the heat transfer surface area, such as heat transfer vanes, radial fins or longitudinal fins, or a multi-lobed balloon surface, collectively referred to as heat exchange fins. In addition, the heat transfer region of the device can be in the form of an expandable balloon, where the balloon remains inflated by, for example, the pressure difference in a fluid flows through an inflow and outflow lumen.

It is estimated that heat exchange device whose surface temperature is controlled between about 1 to 15° C. and may provide a body core cooling rate of approximately 6 to 8° C. per hour in a patient of typical size, for example 115 pounds to 195 pounds and having approximately normal body temperature (37° C.). This estimate is highly dependent on a number of factors including the rate of blood flow through the vessel the initial body temperature of the patient, the external surface area of the device through which heat is transferred, etc. The actual rate achieved may vary substantially from the above estimate. A more helpful estimation of temperature control of the patient's body may be the wattage of energy [heat] removed from the body. At normal blood flows over a catheter as described, as many as 300 watts of energy may be removed from the blood. At rest, the human body generates about 100 watts, but shivering may increase this amount to as much as five fold. The ability to cool the body or control the body's temperature is thus greatly enhanced by the administration of anti-shivering agents while employing the cooling catheter. Other design considerations include a sensitive temperature sensor (see for example, FIG. 23) to closely monitor the temperature of the distal end of the device. While care should be taken to avoid freezing the tissue or fluid or inducing shock to the patient, this is rarely a concern. Since blood is essentially water containing a number of suspended and dissolved substances, its freezing point is somewhat below 0° C.

As may be readily appreciated, the rate of temperature alteration of the patient is greatly dependent on the amount of heat being removed from the blood. This in turn is greatly dependent on the difference in temperature between the blood and the surface of the heat exchange device (ΔT). When it is desirable to rapidly cool the patient, the temperature of the device will be as cold as possible, for example by cooling a heat exchange fluid to almost 0° C., whereas when the operator wants the patient's temperature to remain constant, for example after a state of hypothermia has been reached, only the amount of heat generated by the body in excess of that which is normally lost to the environment needs to be removed. Thus it may be that the temperature of the balloon surface may be maintained near 0° C. during cooling, and as the body reaches the required hypothermic level, the temperature of the heat exchange surface may be maintained just a few degrees below body temperature, for example at about 30° C. once the hypothermic state of 32° C. has been reached.

In heating, it is conservatively accepted that a temperature of a device in contact with the blood may be 42° C. without causing injury to the blood. The ΔT in warming then will generally be less than when the heat exchanger is cooling the blood. If a carefully controlled rate of warming is desired, it will be readily appreciated that a large amount of metabolic heat generated by the body by shivering may overwhelm the system's ability to precisely control the rate of warming. Therefore even when warming a hypothermic patient, control of shivering is important.

Figure 2:
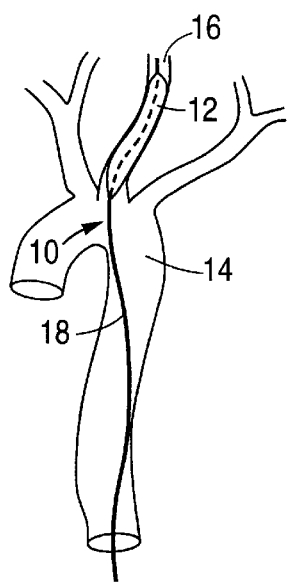
FIG. 2 illustrates a heat exchange device having a heat exchange region positioned within the left common carotid artery.

Some preferred configurations of heat exchange devices are illustrated in the accompanying figures. In FIG. 2, a heat exchange balloon catheter 10 with a finned balloon portion 12 may be positioned within at least a portion of the descending aorta 14 and a blood vessel 16 conducting blood flow to the brain region. The balloon portion 12 is typically formed of material that is sufficiently thin to promote effective thermal transfer between heat exchange fluid within the balloon and blood flowing within heat exchange proximity of the balloon, but which is not excessively elastic to expand and unintentionally obstruct a fluid passageway or blood vessel 16. A particularly suitable material is a thin, strong but relatively inelastic material such as PET (polyethylene terephthalate), which will allow for a predictable balloon configuration with adequate heat exchange properties. The catheter shaft 18 of the thermal catheter 10 may be placed in a desired location relative to a selected body region or artery 16 by conventional techniques such as guiding catheters or steerable wire over-the-wire technique as known to those of ordinary skills in the field. The balloon portion 12 of the catheter 10 may support the closed-loop circulation of a heat transfer fluid within the catheter and balloon as described in the example set forth below. The increased surface area of the inflated balloon may provide effective heat transfer within a body region by thermal conduction, and the configuration of the balloon may further permit continued blood flow without substantial disruption by creating channels exterior of the balloon surface when the balloon is expanded.

Figure 3:
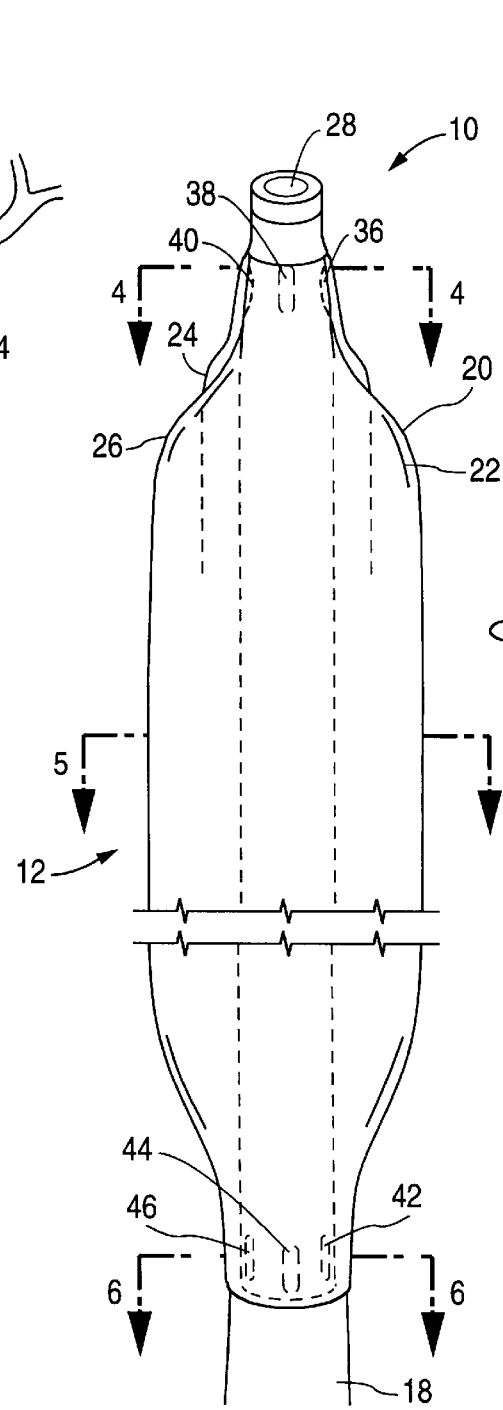
FIG. 3 depicts a heat exchange catheter having a heat exchange balloon and a plurality of heat transfer fins.

FIG. 3 illustrates a heat exchange balloon 12 mounted on a shaft 18, the balloon being defined by a longitudinal axis and a plurality of heat transfer fins 20, 22, 24 and 26 projecting radially outward from the longitudinal axis of the catheter shaft. The heat transfer fins may be formed, for example, as the lobes of a multi-lobed, collapsible balloon. The shaft 18 is generally round and in this embodiment includes a working lumen 28 running through the shaft and open at the distal end of the catheter. Although in a preferred method, the anti-shivering agent is administered by intramuscular or intravenous injection, it may also be administered through the central, or working lumen In one embodiment of the invention, the working lumen is used for the injection of the anti-shivering agent. The working lumen can also serve other functions. For example, along with being provided in combination with an anti-shivering agent, the catheter device may further be provided in combination with a device (such as a guide wire, or embolectomy catheter) or other medicament (such as a thrombolytic agent, a barbiturate, an anticoagulant, a neuroprotectant, an anti-seizure agent, an oxygenated perfusate, a vasodilator, an agent which prevents vasospasm, an agent to prevent platelet activation, and an agent to deter the adhesion of platelets), all of which can be insertion through the working lumen. In addition, the working lumen may be used for the injection of fluoroscopic dye, for the receipt of a guide wire, or as a guiding catheter for various diagnostic or therapeutic devices including, for example, an angioplasty catheter, an embolectomy catheter, an occlusion member delivering catheter, an embolization member delivering catheter, an electro-cautery device, or a microcatheter. As may be appreciated, the use of the lumen for one function does not prevent its subsequent use for another, so it may be used sequentially for several or even all of the uses described here.

Figure 4:
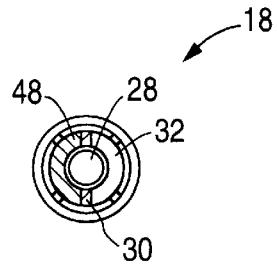
FIG. 4 is a cross-sectional view of the distal end of the catheter taken along line 4—4 of FIG. 3.
Figure 6:
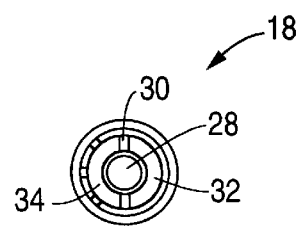
FIG. 6 is a cross-sectional view of the proximal end of the catheter taken along line 6—6 of FIG. 3.

The shaft exterior of the central lumen is shown in FIG. 4 and FIG. 6 as being divided by a web 30 into two channels, an inlet channel 32 and an outlet channel 34. The shaft has inlet orifices 36, 38, 40 (shown in FIG. 3) communicating between the inlet channel and the interior of the balloon at the distal portion of the balloon. The shaft also has outlet orifices 42, 44, 46 communicating between the interior of the balloon and the outlet channel. A plug 48 is inserted in the outlet channel between the inlet and the outlet orifices.

Figure 5:
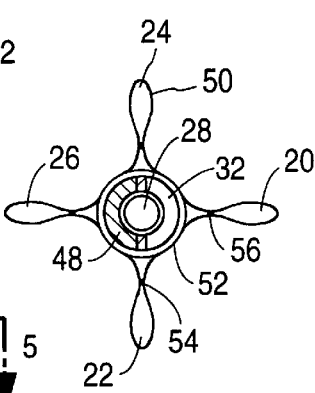
FIG. 5 is a cross-sectional view of the central section of the catheter taken along line 5—5 of FIG. 3.

The balloon 12 may be made of, for example, a single sheet of collapsible thin plastic material 50, as shown in FIG. 5 sufficiently thin to allow for effective thermal exchange between a heat exchange fluid on the interior of the balloon and blood flowing over the exterior of the balloon. Tacking the material to the shaft as shown at 52 may form lobes of the balloon. Tacking the sheet of plastic to itself in appropriate locations as shown at 54 and 56 may further shape the lobes. The lobed shape of the balloon surface provides a significant surface area for heat exchange while also providing for continued flow past the balloon through the space between the lobes of the balloon.

In operation, heat exchange fluid (not shown) is pumped under pressure into the inlet channel 32. Suitable heat exchange fluids include, by way of illustration and not limitation, sterile saline or other biocompatible fluid with appropriate heat transfer characteristics. The heat exchange fluid flows down the inlet channel until it reaches the inlet orifices 36, 38, 40 at the distal end of the balloon. The fluid flows from the inlet channel into the interior of the balloon. It then flows in a proximal direction through the interior of the balloon until it reaches the outlet orifices 42, 44, 46 at the proximal end of the balloon. The heat exchange fluid then flows from the interior of the balloon through the outlet orifices and into the outlet channel 34 where it then flows back down the shaft and out of the body. In this manner, the heat exchange fluid absorbs heat from the blood flowing in heat transfer proximity to the balloon.

Figure 7:
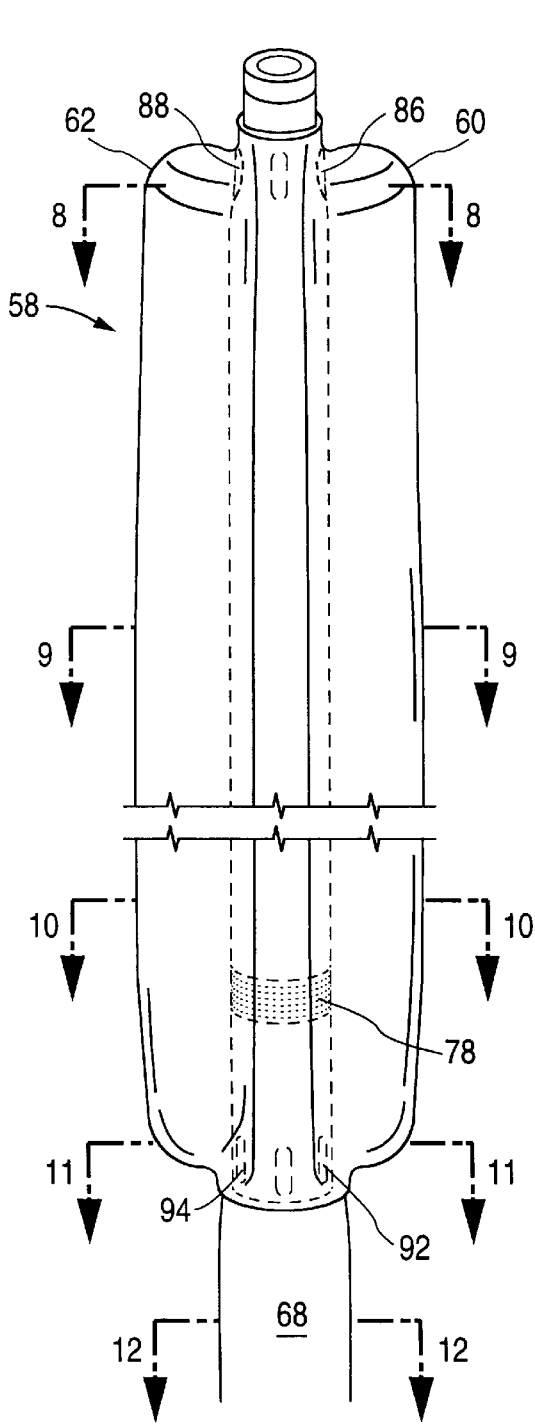
FIG. 7 illustrates an alternative construction of a heat exchange catheter.
Figure 12:
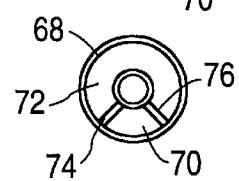
FIG. 12 is a cross-sectional view of the proximal shaft of the catheter taken along line 12—12 of FIG. 7.

An alternative construction to the heat exchange balloon is shown in FIG. 7 wherein the heat exchange region is formed using a series of three collapsible balloon lobes 60, 62, 64 located around a central collapsible lumen 66. A proximal shaft 68 is formed having two channels, an inlet channel 70 and an outlet channel 72. The interior of the shaft is divided into two lumens by webs 74 and 76, as shown in FIG. 12, but the lumens do not occupy equal portions of the interior of the shaft. The inlet channel occupies about ⅓ of the circumference of the interior; the outlet channel occupies about ⅔ of the circumference of the interior for reasons that will be explained below.

Figure 8:
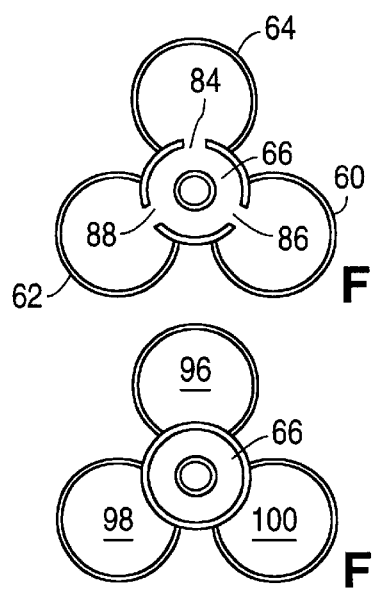
FIG. 8 is a cross-sectional view of the distal end of the catheter taken along line 8—8 of FIG. 7.
Figure 9:
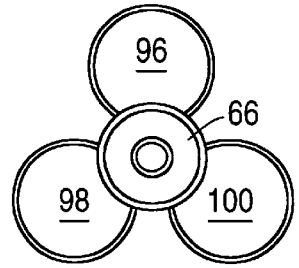
FIG. 9 is a cross-sectional view of a portion of the central section of the catheter taken along line 9—9 of FIG. 7.
Figure 10:
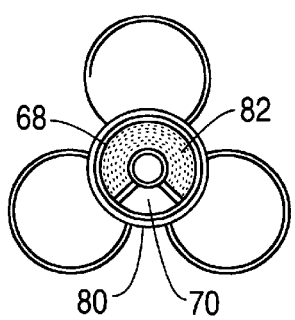
FIG. 10 is a cross-sectional view of another portion of the central section of the catheter taken along line 10—10 of FIG. 7.
Figure 11:
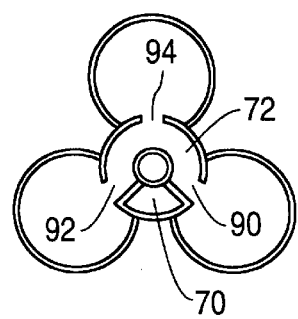
FIG. 11 is a cross-sectional view of the proximal end of the catheter taken along line 11—11 of FIG. 7.

At the heat exchange region of the catheter, a transition 78 is formed between the shaft 68 and the tube 80 forming the central collapsible lumen 66. The outlet channel is plugged 82, as shown in FIG. 10, the tube 80 is affixed over the shaft 68 by, for example gluing, at the transition 78, and the shaft ends with the tube (not shown). In this way, as shown in FIG. 9, the inlet channel in this portion of the catheter occupies the entire circumference of the shaft. At the distal end of the balloon, shown in FIG. 8, inlet orifices 84, 86, 88 are formed between the inlet channel and the three collapsible balloons. At the proximal end of the heat exchange region, shown in FIG. 11, outlet orifices 90, 92, 94 are formed between the interior of each balloon and the outlet channel in the shaft. The configuration of the outlet channel is such that communication with the interior of each of the three balloons is possible.

In operation, heat exchange fluid flows down the inlet channel in the shaft 70, continues down lumen 66 to the distal end of the heat exchange region, exit the lumen through the inlet orifices 84, 86, 88 to the interior lumens of the balloon lobes 96, 98, 100, travel back down each of the three balloons and re-enter the shaft through the outlet orifices 90, 92, 94 and then down the outlet channel 72 toward the proximal end of the catheter. In this way heat exchange fluid may be circulated through the three balloons to remove heat from the blood flowing in heat transfer proximity to the balloons. The material from which the balloons are made is made of a material that will permit significant thermal exchange between the heat exchange fluid on the interior of the balloon and the body fluid such as blood flowing in heat exchange proximity to the surface of the balloon. A particularly suitable material is very thin plastic material, which may also be made strong enough to withstand the pressure necessary for adequate flow of the heat exchange fluid.

FIG. 13 illustrates another heat exchange catheter 102 suitable for use in the method of this invention. The catheter 102 is constructed by attaching a balloon 104 having multiple lumens, over an inner shaft member 106 in the manner described below. The assembled catheter 102 (FIG. 13) has a four-lumen thin-walled balloon 104 (FIG. 15) which is attached over an inner shaft 106 (FIG. 14).

The cross-sectional view of the four-lumen balloon taken along line 16—16 of FIG. 15 is shown in FIG. 16. The four-lumen thin-walled balloon 104 has three outer lumens 108, 110 and 112, which are wound around an inner lumen 114 in a helical pattern. All four lumens are thin walled balloons and each outer lumen shares a common thin wall segment (116, 118, 120) with the inner lumen 114. The balloon is approximately twenty-five centimeters long and when installed, both the proximal end 122 and the distal end 124 are sealed around the shaft 106 in a fluid tight seal.

The shaft 106 is attached to a hub 126 at its proximal end. The cross-sectional view of the proximal shaft at line 17—17 in FIG. 14 is shown at FIG. 17. The interior configuration of the shaft has three lumens: a guide wire lumen 128, an inflow lumen 130 and an outflow lumen 132. It is understood however, the lumens 130 and 132 are referred to as inflow and outflow for illustrative purposes only. One of skill in the art may readily appreciate that lumen 132 may be used as the inflow lumen and lumen 130 may be used as the outflow lumen if the flow of the heat exchange fluid is reversed.

At the hub 126, the guide wire lumen 128 communicates with a guide wire port. 134, the inflow lumen 130 is in fluid communication with an inflow port 136, and the outflow lumen 132 is in communication with an outflow port 138. Attached at the hub 126 and surrounding a portion of shaft 106 is a length of strain relief tubing 140 which may be, for example, shrink tubing.

Between the strain relief tubing 140 and the proximal end 122 of the balloon, the shaft 106 is at the extruded outer diameter of about 0.118 inches. The internal configuration is as shown in FIG. 17. Immediately proximal of the balloon attachment at its proximal end 22, the shaft has a necked down section 142. The outer diameter of the shaft is reduced to about 0.10 to 0.11 inches, but the internal configuration of the lumens is maintained. Compare, for example, the shaft cross-section shown in FIG. 17 with the cross-section shown in FIG. 18 or the shaft cross-section shown in FIG. 20. This length of reduced diameter shaft remains at approximately constant diameter between the first necked down section 142 and a second necked down section 144.

Immediately distal of the necked down section 142, a proximal balloon marker band 146 is attached around the shaft. The marker band 146 is a radiopaque material such as a platinum band or radiopaque paint, and is useful for locating the proximal end of the balloon by means of fluoroscopy while the catheter is within the body of the patient.

At the marker band 146, the distal end of all four lobes of the balloon (108, 110, 112, 114) at 122 are fastened to the inner member 122. This may be accomplished by folding the balloon down around the shaft, placing a sleeve, for example a short length of tubing, over the balloon and inserting adhesive, for example by wicking the adhesive around the entire inner circumference of the sleeve. This simultaneously fastens the balloon down around the shaft, and creates a fluid tight seal at the proximal end of the balloon.

Distal of this seal, under the balloon, a window 148 is cut through the wall of the outflow lumen in the shaft. Juxtaposed to that window, a plurality of slits 150 are cut into the wall of the outer balloon lumen, as shown in the cross-sectional view of FIG. 18 and the view in FIG. 19. Because the outer lumens are twined about the inner lumen in a helical fashion, each of the outer tubes passes over the outflow lumen of the inner shaft member at a slightly different location along the length of the inner shaft, and where each of the other two outer lumens pass over the outflow lumen of the shaft, other windows (152, 154) are cut into the outflow lumen and a plurality of slits (156, 158) are cut into the outer lumen to fluidly connect the proximal portion of that outer lumen to the outflow lumen of the shaft. See, for example, the section of FIG. 13 immediately distal of line 18—18. In this way the proximal portion of each outer lumen (108, 110, 112) is fluidly connected to the outflow lumen of the shaft.

Distal of the windows in the outflow lumen, the inner lumen 114 of the four lumen balloon is sealed around the shaft in a fluid tight seal. The outflow lumen 132 is plugged 160, and the wall to the inflow lumen is removed, as shown in FIG. 20. This may be accomplished by the necked down section 144 to seal the outflow lumen shut (plug 160), removing the wall 162 of the inflow lumen 130, and affixing the wall of the inner lumen of the balloon around the entire outside 164 of the shaft with adhesive. The adhesive will also act as a plug to prevent the portion of the inner lumen proximal of the plug from being in fluid communication with the inner member distal of the plug.

Just distal of the necked down section 144, the guide wire lumen 128 of the shaft may be terminated and joined to a guide wire tube 166. The tube 166 then continues to the distal end of the catheter. The inflow lumen 130 is open into the inner lumen of the four-lobed balloon and thus in fluid communication with that lumen.

The distal end 124 of the balloon 104 including all four lumens of the balloon is sealed down around the guide wire tube 166 in a manner similar to the way the balloon is sealed at the proximal end around the shaft. This seals all four lumens of the balloon in a fluid tight seal. Just proximal of the seal, a plurality of slits 168 are cut into the common wall between each of the three outer lumens 108, 110, 112, of the balloon and the inner lumen 144 so that each of the outer lumens is in fluid communication with the inner lumen, as is shown in FIG. 21 and the cross-sectional view of FIG. 22.

Just distal of the balloon, near the distal seal, a distal marker band 170 is placed around the inner shaft. A flexible length of tube 172 may be joined onto the distal end of the guide wire tube 166 to provide a flexible tip to the catheter. The distal end 174 of the flexible tube 172 is open so that a guide wire may exit the tip. Medicine or radiographic fluid may also be injected distal of the catheter through the guide wire lumen.

In use, the catheter 102 is inserted into the body of a patient so that the balloon is within a blood vessel. Heat exchange fluid is circulated into the inflow port 136, travels down the inflow lumen 130 and into the inner lumen 114 at the wall 162 at the end of the inflow lumen. The heat exchange fluid travels to the distal end of the inner lumen and through the slits 168 between the inner lumen 114 and the outer lumens 108, 110 and 112.

The heat exchange fluid then travels back through the three outer lumens of the balloon to the proximal end of the balloon. The outer lumens are wound in a helical pattern around the inner lumen. At some point along the proximal portion of the shaft, each outer lumen is located over the portion of the shaft having a window (154, 152, 148) to the outflow lumen and the outer balloon lumens have a plurality of slits (158, 156, 150) that are aligned with the windows. The heat transfer fluid passes through the slits (158, 156, 150) through the windows (154, 152, 148) and into the outflow lumen 132. From there it is circulated out of the catheter through the outflow port 138.

Counter-current circulation between the blood and the heat exchange fluid is highly desirable for efficient heat exchange between the blood and the heat exchange fluid. Thus if the balloon is positioned in a vessel where the blood flow is in the direction from the proximal toward the distal end of the catheter, for example if it were placed from an insertion point in the femoral vein into the ascending vena cava, it is desirable to have the heat exchange fluid in the outer balloon lumens flowing in the direction from the distal end toward the proximal end of the catheter, as is the arrangement describe above. It is to be readily appreciated, however, that if the balloon were placed so that the blood was flowing along the catheter in the direction from distal to proximal, for example if the catheter was placed into the ascending vena cava from an insertion point in the jugular vein, it would be desirable to have the heat exchange fluid circulate in the outer balloon lumens from the proximal end to the distal end. This could be accomplished by merely reversing which port is used for inflow direction and which for outflow.

In use, a physician may employ the method of the invention to place a patient in a hypothermic state. By use of the Seldinger technique, the physician may insert a heat exchange catheter having a heat exchange balloon into the femoral vein of the patient. The catheter is advanced until the heat exchange balloon is located in the inferior vena cava. The physician then utilizes the heat exchange system to circulate cold saline through the heat exchange balloon, which removes heat from the blood flowing past the heat exchange balloon. The physician continues to utilize the heat exchange system for a sufficient length of time to reduce the temperature of the patient.

Simultaneously the physician administers an α2-adrenoreceptor agonist, non-opiod analgesic monoamine uptake inhibitor or neuropeptide in the manner and at the dosage/duration as described above. The physician may administer a bolus amount of the anti-shivering agent and subsequent maintenance amounts of the agent, or may administer the agent in any other effective manner. In any event, when the patient's temperature falls below the shivering threshold, the level of anti-shivering agent in the patient will be sufficient to reduce shivering. This in turn makes the reduction in temperature by the heat exchange system more effective, and reduces the discomfort and other adverse effects of shivering.

When the patient has reached the target temperature below the shivering threshold, the level of anti-shivering agent is maintained at an effective level, so that the heat exchange system can maintain the patient precisely at the target temperature. The system has one or more patient temperature monitors that provide feedback to the control unit for the system. Since the amount of metabolic heat generated by the body is reduced, and since the thermoregulatory mechanisms of the body are not actively opposing the temperature control of the heat exchange system by shivering, the target temperature can more safely and more precisely maintain the patient at the target temperature.

When the physician wishes to re-warm a patient slowly from a hypothermic condition below the shivering threshold, he or she may employ the method of the invention to more precisely control the rate of warming. When the patient has an effective level of anti-shivering agent so as to reduce shivering, the physician may activate the heat exchange system to begin in vivo core warming. The feedback from the patient temperature monitors allows control of the heat exchange system to slowly warm the patient, or to slightly cool the blood of the patient if the patient's own body is functioning to warm the patient too fast. Because the very effective shivering mechanism is reduced or eliminated, the heat exchange system has sufficient power and precision to maintain the gentle rate of warming and prevent the body from re-warming too fast.

In each of the above examples, the anti-shivering agent can be administered before the heat exchange begins, or may be administered only upon the initiation of shivering, or any appropriate manner.

Each of the patents, publications, and other published documents mentioned or referred to in this specification is herein incorporated by reference in its entirety.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Accordingly, the scope of the invention should therefore be determined with reference to the appended claims, along with the full range of equivalents to which those claims are entitled.

What is claimed is:

1. A method for controlling the temperature of all or a portion of a patient's body to a temperature below its set point temperature, while reducing shivering, comprising the steps of: (a) sensing the temperature of all or a portion of the patient's body; (b) generating a signal based upon said sensed temperature; (c) controlling the temperature of all or a portion of the patient's body based upon said signal; and (d) administering an agent selected from the group consisting of α2-adrenoteceptor agonists, non-opiod analgesic monoamine uptake inhibitors and neuropeptides to said patient.

2. The method of claim 1 wherein said α2-adrenoreceptor agonist is selected from the group consisting of dexmedetomidine; detomidine; medetomidine; clonidine; bromonidine; tizanidine; mivazerol; guanfacine; oxymetazonline; (R)-(-)-3'-(2-amino-1-hydroxyethyl)-4'-fluoro-methanesulfoanilide; 2-[(5-methylbenz-1-ox-4-azin-6-yl)imino]imidazoline; 5-bromo-N-(4,5-dihydro-1H-imidazol-2-yl)-6-quinoxalinamine; 5,6,7,8-tetrahydro-6-(2-propenyl)-4H-thiazolo[4,5-d]azepin-2-amine; 6-ethyl-5,6,7,8-tetrahydro-4H-oxaazolo[4,5-d]azepin-2-amine; 5,6-dihydroxyl-1,2,3,4-tetrahydro-1-naphyl-imidazoline; and pharmaceutically acceptable salts thereof.

3. The method of claim 2 wherein said α2-adrenoreceptor agonist is dexmedetomidine or a pharmaceutically acceptable salt thereof.

4. The method of claim 1 wherein said non-opiod analgesic monoamine uptake inhibitor is selected from the group consisting of nepofam; tramadol; and pharmaceutically acceptable salts thereof.

5. The method of claim 4 wherein said non-opiod analgesic monoamine uptake inhibitor is nepofam or a pharmaceutically acceptable salt thereof.

6. The method of claim 1 wherein said neuropeptide is selected from the group consisting of neurotensin; neurotensin analogs; bombesin; neuromedin; dermorphin; D-ala-deltorphin; and pharmaceutically acceptable variants thereof.

7. The method of claim 6 wherein said neuropeptide is neurotensin or a pharmaceutically acceptable variant thereof.

8. The method of claim 1 wherein the temperature controlling step (c) includes lowering the temperature below the set point temperature.

9. The method of claim 1 wherein the temperature controlling step (c) includes raising the temperature from an initial temperature below the set point temperature.

10. The method of claim 9 wherein the temperature controlling step (c) includes raising the temperature at a predetermined rate.

11. The method of claim 9 wherein the temperature controlling step (c) includes maintaining the temperature at a stable temperature below the set point temperature.

12. The method of claim 11 wherein the stable temperature is normothermia.

13. The method of claim 1 wherein the temperature controlling step (c) includes placing a heat exchange device having a heat exchange region into the vascular system of the patient and controlling the temperature of the heat exchange region for a sufficient time to affect the temperature of all or a portion of the patient's body.

14. The method of claim 13 wherein the heat exchange device is a catheter and the heat exchange region comprises a balloon on said catheter, the temperature of said balloon being controlled by the circulation of a heat exchange fluid through the interior of said balloon.

15. A method of controlling the temperature of a patient below the set point temperature comprising the steps of: (a) employing internal in vivo core temperature regulation; and (b) administration of an agent selected from the group consisting of α2-adrenoreceptor agonists, non-opiod analgesic monoamine uptake inhibitors and neuropeptides.

16. The method of claim 15 wherein said α2-adrenoreceptor agonist is selected from the group consisting of dexmedetomidine; detomidine; medetomidine; clonidine; bromonidine; tizanidine; mivazerol; guanfacine; oxymetazonline; (R)-(-)-3'-(2-amino-1-hydroxyethyl)-4'-fluoro-methanesulfoanilide; 2-[(5-methylbenz-1-ox-4-azin-6-yl)imino]imidazoline; 5-bromo-N-(4,5-dihydro-1H-imidazol-2-yl)-6-quinoxalinamine; 5,6,7,8-tetrahydro-6-(2-propenyl)-4H-thiazolo[4,5-d]azepin-2-amine; 6-ethyl-5,6,7,8-tetrahydro-4H-oxaazolo[4,5-d]azepin-2-amine; 5,6-dihydroxyl-1,2,3,4-tetrahydro-1-naphyl-imidazoline; and pharmaceutically acceptable salts thereof.

17. The method of claim 16 wherein said α2-adrenoreceptor agonist is dexmedetomidine or a pharmaceutically acceptable salt thereof.

18. The method of claim 15 wherein said non-opiod analgesic monoamine uptake inhibitor is selected from the group consisting of nepofam; tramadol; and pharmaceutically acceptable salts thereof.

19. The method of claim 18 wherein said non-opiod analgesic monoamine uptake inhibitor is nepofam or a pharmaceutically acceptable salt thereof.

20. The method of claim 15 wherein said neuropeptide is selected from the group consisting of neurotensin; neurotensin analogs; bombesin; neuromedin; dermorphin; D-ala-deltorphin; and pharmaceutically acceptable variants thereof.

21. The method of claim 20 wherein said neuropeptide is neurotensin or a pharmaceutically acceptable variant thereof.

22. The method of claim 15 wherein the step of employing internal in vivo core temperature regulation comprises placing a heat exchange device in the blood vessels of the patient, said heat exchange device having a heat exchange region, said heat exchange region being in contact with the flowing blood of the patient; and controlling the temperature of the heat exchange region for a sufficient time to affect the temperature of the patient.

23. The method of claim 15 wherein the heat exchange device is a catheter having a shaft for the circulation of heat exchange fluid therein, and said heat exchange region is a balloon; and said step of controlling the temperature of the heat exchange region includes circulation of heat exchange fluid through said shaft and through the interior of said balloon.

* * * * *